(12) United States Patent
Yanuma

(10) Patent No.: US 8,267,873 B2
(45) Date of Patent: Sep. 18, 2012

(54) GUIDEWIRE CATHETER

(75) Inventor: Yutaka Yanuma, Tokyo (JP)

(73) Assignee: Olympus Medical Systems Corp. (JP)

( * ) Notice: Subject to any disclaimer, the term of this patent is extended or adjusted under 35 U.S.C. 154(b) by 791 days.

(21) Appl. No.: 12/202,494

(22) Filed: Sep. 2, 2008

(65) Prior Publication Data

US 2010/0056910 A1  Mar. 4, 2010

(51) Int. Cl.
*A61B 5/025* (2006.01)
*A61B 1/00* (2006.01)
*A61M 31/00* (2006.01)

(52) U.S. Cl. .................. 600/585; 604/516; 600/107

(58) Field of Classification Search .............. 600/433, 600/434, 435, 466, 585; 604/102, 264, 508, 604/523, 528, 544; 607/122
See application file for complete search history.

(56) References Cited

U.S. PATENT DOCUMENTS

| | | | |
|---|---|---|---|
| 5,395,335 A * | 3/1995 | Jang .................. | 604/102.02 |
| 5,570,701 A | 11/1996 | Ellis et al. | |
| 5,634,475 A * | 6/1997 | Wolvek .................. | 600/585 |
| 5,891,105 A * | 4/1999 | Mahurkar ............... | 604/195 |
| 6,066,151 A * | 5/2000 | Miyawaki et al. ....... | 606/169 |
| 6,193,735 B1 | 2/2001 | Stevens | |
| 6,520,951 B1 * | 2/2003 | Carrillo et al. ........... | 600/585 |
| 2001/0029374 A1 * | 10/2001 | Kikuchi et al. .......... | 606/61 |
| 2004/0153050 A1 * | 8/2004 | Heller et al. ............. | 604/528 |
| 2005/0043618 A1 * | 2/2005 | Mansouri-Ruiz ........ | 600/435 |
| 2005/0049455 A1 * | 3/2005 | Ootawara et al. ........ | 600/107 |
| 2005/0240120 A1 | 10/2005 | Modesitt | |
| 2007/0239066 A1 * | 10/2007 | Laham et al. ............. | 600/567 |

FOREIGN PATENT DOCUMENTS

| | | |
|---|---|---|
| JP | 8-257134 | 10/1996 |
| JP | 2003-79741 | 3/2003 |
| WO | WO 2007/082216 A1 | 7/2007 |

OTHER PUBLICATIONS

Search Report issued by European Patent Office in connection with corresponding European application No. EP 09 01 0880 on Jan. 13, 2010.

* cited by examiner

*Primary Examiner* — Max Hindenburg
*Assistant Examiner* — Mehari Kidanemariam
(74) *Attorney, Agent, or Firm* — Ostrolenk Faber LLP

(57) ABSTRACT

A guidewire catheter includes: a sheath for passing a guidewire therethrough; an operation section connected to an end of the sheath and having a through-hole for passing the guidewire therethrough; a guidewire adapter connected to the operation section and capable of freely extending or retracting relative to the operation section along the axial line of the through-hole, the guidewire adapter grasping the outer periphery surface of the guidewire projecting from the through-hole, and the guidewire adapter being capable of guiding and moving the guidewire relative to the operation section in an axial direction and a circumferential direction of the through-hole; a bar-shaped slide section formed on one of the operation section and the guidewire adapter in the exterior of the through-hole, the slide section being disposed along a line which is parallel with the axial line of the through-hole; a receiver formed on the other one of the operation section and the guidewire adapter and being capable of moving and supporting the freely extendable or retractable slide section; a connection section having a second through-hole formed coaxially with the axial line of the through-hole formed in the guidewire adapter; and a grip section, engaged with the second through-hole, for grasping an outer periphery surface of the guidewire, and the grip section being capable of freely rotatable around the axial line of the second through-hole.

6 Claims, 22 Drawing Sheets

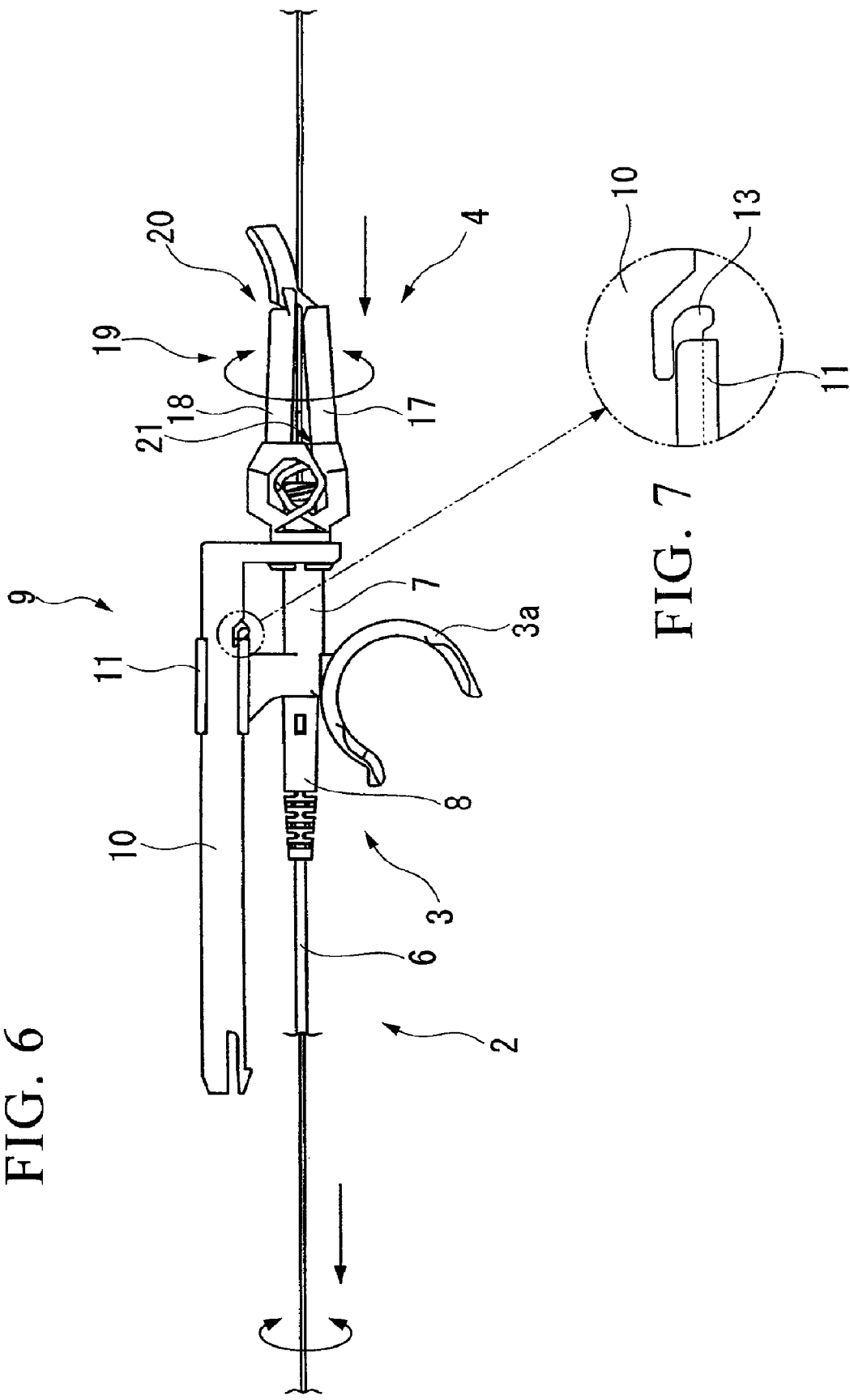

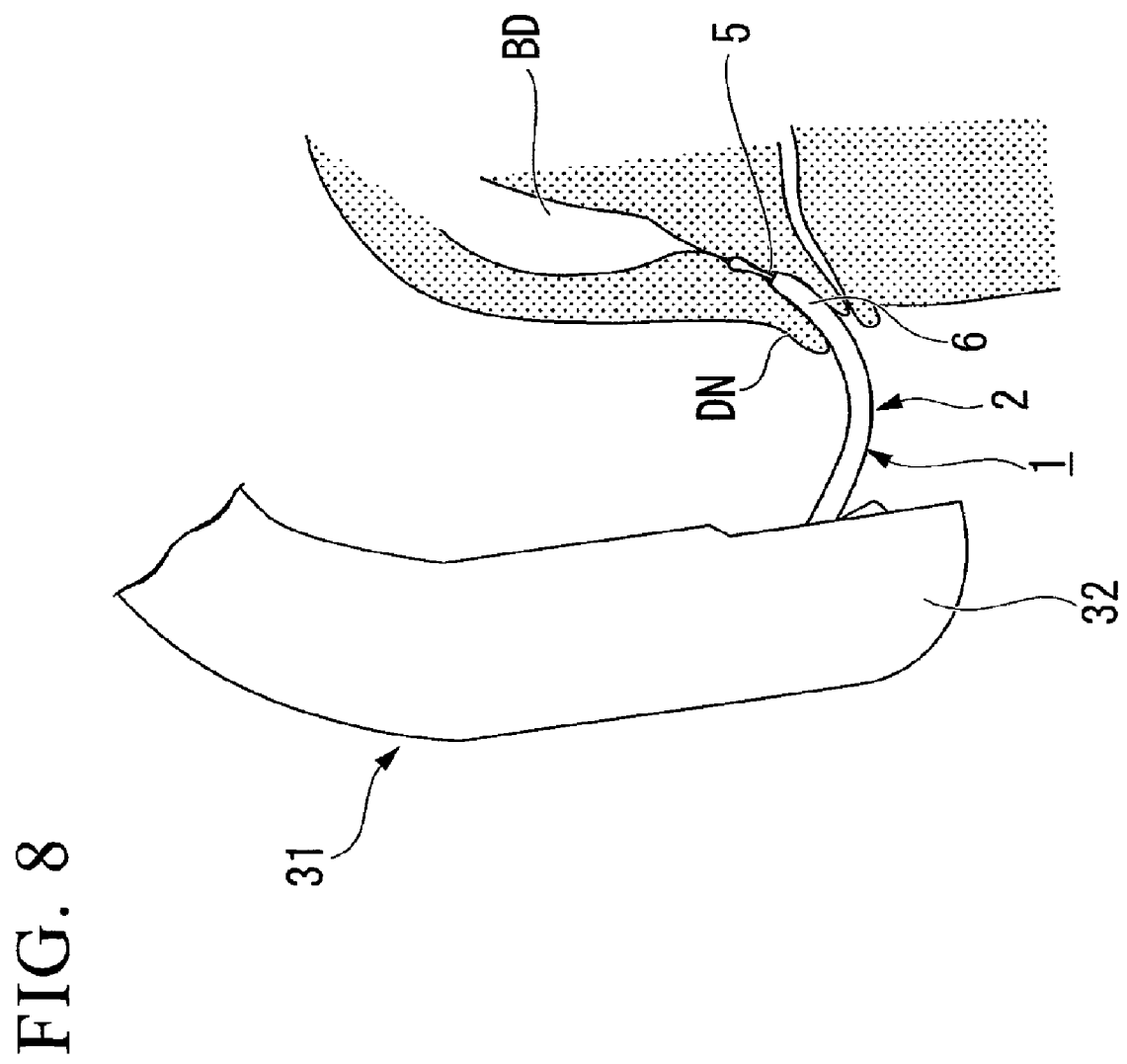

GUIDEWIRE CATHETER

BACKGROUND OF THE INVENTION

1. Field of the Invention

The present invention relates to a guidewire catheter for use with a guidewire for guiding a catheter. More specifically, the present invention relates to a guidewire catheter for use with an adapter for assisting the insertion or the rotation of a guidewire for guiding a catheter endoscopically inserted into a body cavity and used for regressively injecting liquid into a bile duct or a pancreatic duct.

2. Background Art

Endoscopic retrograde cholangiopancreatography (ERCP) is a conventionally-known diagnostic method for finding an abnormality in a pancreas, a cholecyst, or a bile duct. The ERCP provides X-ray photography by inserting a catheter into the nipple of a duodenum and subsequently injecting a contrast agent directly into a pancreatic duct or a bile duct.

However, in some cases, the insertion of the catheter into the bile duct is difficult when the entrance of the nipple is narrow, or when the bile duct is bending. Pushing the catheter into the entrance of the nipple with an excessive force in this case may cause endema on the mucosa thereof, thereby resulting in a further narrowing the entrance.

A contrast agent injected from the catheter upon being entered deeper relative to the mucosa and blocking a port of the pancreatic duce may prevents the drainage of pancreatic fluid, thereby increasing the possibility of developing pancreatitis therein. To address this, a conventional method for finding a bile duct uses a guidewire having a relatively bendable flexible distal end while being projected from the distal end of the catheter by 2 to 3 millimeters.

Some known apparatuses for guiding a catheter in such operations use a guidewire having a diameter smaller than a catheter. For example, Japanese Unexamined Patent Application, First Publication No. H8-257134 discloses an operation assistant instrument for a medical-use guidewire which assists the insertion of a guidewire into a hollow organ.

The operation assistant instrument for the medical-use guidewire having a groove capable of approaching to or separating from each other in the axial direction is designed to allow a guidewire to be inserted into the groove and to fix the medical-use guidewire in the operation assistant instrument. The operation assistant instrument for use with the medical guidewire is capable of attaching the operation assistant instrument to the guidewire, changing the position of the operation assistant instrument, and easily detaching of the guidewire from the operation assistant instrument. In addition, the operation assistant instrument is capable of inserting the guidewire into the lumen of an object tissue by extending or retracting the guidewire, or by rotating the guidewire around the axial line.

SUMMARY OF THE INVENTION

A first aspect of the present invention is a guidewire catheter which includes: a sheath for passing a guidewire therethrough; an operation section connected to an end of the sheath and having a through-hole for passing the guidewire therethrough; a guidewire adapter connected to the operation section and capable of freely extending or retracting relative to the operation section along an axial line of the through-hole, the guidewire adapter grasping the outer periphery surface of the guidewire projecting from the through-hole, and the guidewire adapter being capable of guiding and moving the guidewire relative to the operation section in an axial direction and a circumferential direction of the through-hole; a bar-shaped slide section formed on one of the operation section and the guidewire adapter in the exterior of the through-hole, the slide section being disposed along a line which is parallel with the axial line of the through-hole; a receiver formed on the other one of the operation section and the guidewire adapter and being capable of moving and supporting the freely extendable or retractable slide section; a connection section having a second through-hole formed coaxially with the axial line of the through-hole; and a grip section, engaged with the second through-hole, for grasping an outer periphery surface of the guidewire, and the grip section being freely rotatable around the axial line of the second through-hole.

A second aspect of the present invention is a guidewire catheter which includes: a sheath for passing a guidewire therethrough; an operation section connected to an end of the sheath and having a through-hole for passing the guidewire therethrough; and a guidewire adapter connected to the operation section and capable of freely extending or retracting relative to the operation section along the axial line of the through-hole, the guidewire adapter grasping the outer periphery surface of the guidewire projecting from the through-hole, and the guidewire adapter being capable of guiding and moving the guidewire relative to the operation section in an axial direction and a circumferential direction of the through-hole, wherein the guidewire adapter includes: a cylindrical main unit passing the guidewire adapter therethrough and being capable of communicating with the inside of the sheath; a seal mechanism, connected to a proximal end section of the main unit and passing the guidewire therethrough, for sealing a proximal opening formed on the main unit; a sideport communicating with a space in the sheath and the seal mechanism; a pair of arms connected to the seal mechanism and opposed in a radial direction in the exterior in a circumferential direction of the guidewire, the pair of arms each having a fixture surface for grasping the guidewire, and the pair of arms being capable of swaying so that the pair of fixture surfaces approach to or separate from each other; and a hook for fixing the pair of arms while the guidewire is compressed and fixed by the fixture surfaces, wherein the seal mechanism includes: a seal member made of an elastic member and provided to the proximal end of the main unit; and a pusher having a link mechanism disposed proximally relative to the seal member and connected to at least one of the pair of arms, and wherein the pusher linking with swayable movement of the pair of arms compresses the seal member.

A third aspect of the present invention is a guidewire catheter which includes: a sheath for passing a guidewire therethrough; an operation section connected to an end of the sheath and having a through-hole for passing the guidewire therethrough; a guidewire adapter connected to the operation section and capable of freely extending or retracting relative to the operation section along the axial line of the through-hole, the guidewire adapter grasping the outer periphery surface of the guidewire projecting from the through-hole, and the guidewire adapter being capable of guiding and moving the guidewire relative to the operation section in an axial direction and a circumferential direction of the through-hole; a bar-shaped slide section formed on one of the operation section and the guidewire adapter in the exterior of the through-hole, the slide section being disposed along a line which is parallel with the axial line of the through-hole; a receiver formed on the other one of the operation section and the guidewire adapter and being capable of moving and supporting the freely extendable or retractable slide section; a connection section having a second through-hole formed coaxially with the axial line of the through-hole; a grip section, engaged with the second through-hole, for grasping an outer periphery surface of the guidewire, and the grip section being freely rotatable around the axial line of the second through-hole; a first incised section formed by incising an outer wall section of the connection section in the axial direction thereof, and a second incised section formed by incising an outer wall section of the grip section in the axial direction thereof, wherein rotational positions of the first incised section and the second incised section are variable between a connecting state or a disconnecting state of the connection section with respect to the grip section.

BRIEF DESCRIPTION OF DRAWINGS

FIG. 6 shows the guidewire catheter in use.

FIG. 7 shows a click section when the guidewire catheter is used.

FIG. 8 shows a process of maneuver in the ERCP using the guidewire catheter.

PREFERRED EMBODIMENTS

A guidewire catheter according to a first embodiment of the present invention will be explained with reference to FIGS. 1 to 9 as follows.

Figure 1:
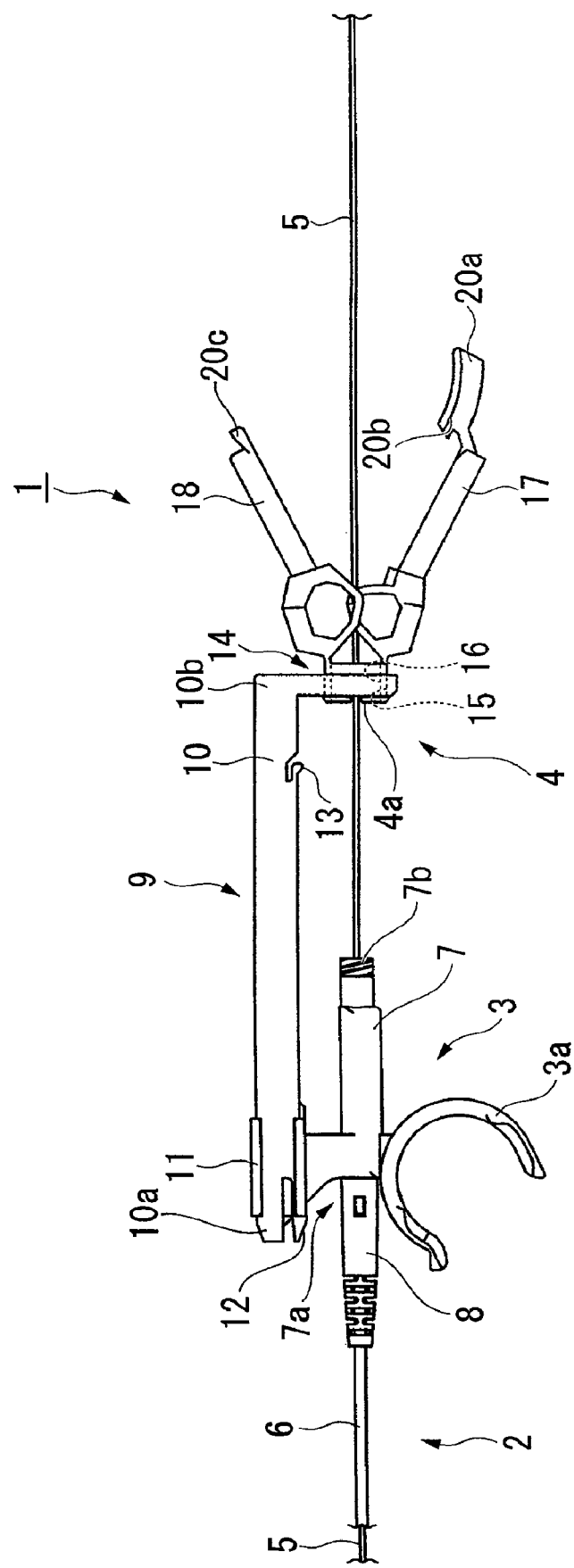
FIG. 1 shows a guidewire catheter according to a first embodiment of the present invention.

FIG. 1 shows a guidewire catheter 1 according to the present embodiment. The guidewire catheter 1 is provided with: an insertion section 2 which will be inserted into a body via an endoscope; an operation section 3 connected to the insertion section 2; and a guidewire adapter 4 connected to the operation section 3.

The insertion section 2 is a tubular sheath 6 allowing the guidewire 5 to be inserted therethrough and to extend or retract freely therethrough. While a guidewire has various outer diameters, the most commonly used outer diameter of the guidewire is, for example, 0.035 inch (0.89 mm); and the appropriate range of the inner diameter of sheath 6 in this case is 0.9 mm to 1.2 mm. The guidewire may have more reduced outer diameters such as 0.025 inch (0.64 mm) or 0.018 inch (0.46 mm); and the appropriate ranges of inner diameter of sheaths in these cases may be 0.7 mm to 0.8 mm and 0.5 mm to 0.6 mm respectively.

In addition, the space in the sheath 6 is designed to not only allow the guidewire 5 to be inserted therethrough but also supply various kinds of liquid including contrast agent or physiological saline.

The operation section 3 is provided with a cylinder section 7 which allows the guidewire 5 to be inserted therethrough and to extend or retract freely therethrough. A connection port 7a is formed around the outer periphery of one end of the cylinder section 7. The sheath 6 connected to the connection port 7a is further inserted through the connection port 7a. An end of a bend-proof pipe 8 can be fixed to the connection port 7a.

A port 7b, which is a part of a commonly-known leur lock mechanism, is formed around the outer periphery of the other end of the cylinder section 7. The port 7b is designed to allow an end of a liquid-supply instrument including a syringe or the like that is adaptable to the leur lock mechanism to be connected thereto directly or via an appropriate adapter.

Figure 3:
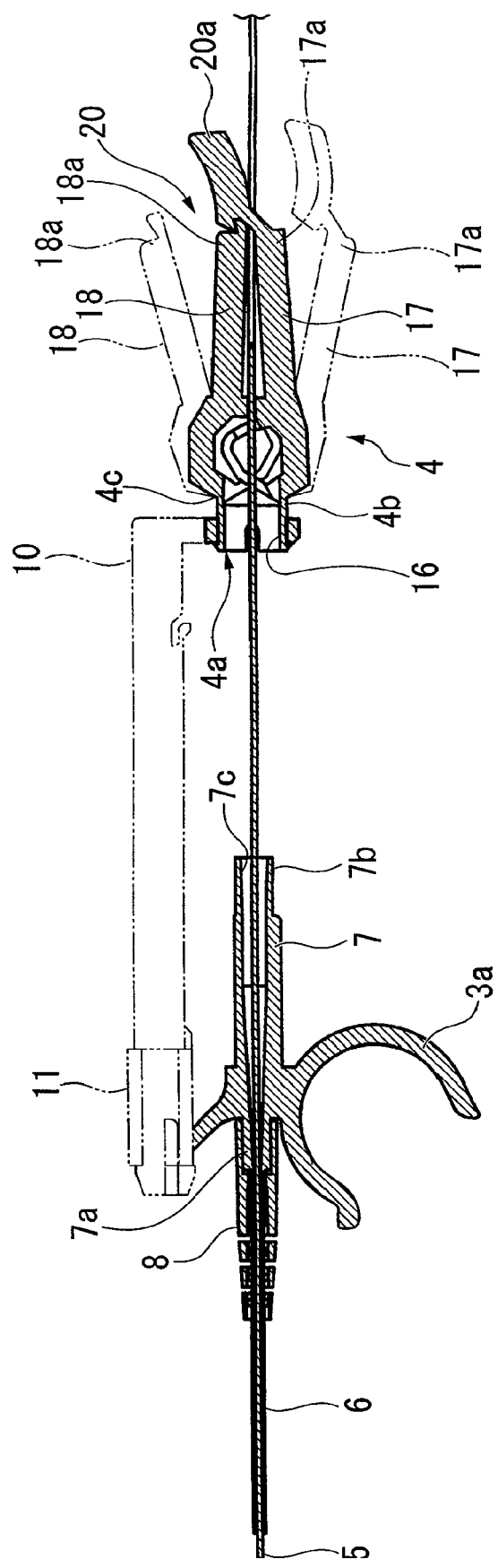
FIG. 3 is a fragmentary sectional view of the guidewire catheter.

In addition, a through-hole 7c is formed in the cylinder section 7 along the axial line (see FIG. 3). The inner wall section therein has an inner diameter which increases from the connection port 7a to the port 7b.

In addition, a coupler section 3a which is connectible with an endoscope or the like is formed on the operation section 3.

The operation section 3 and the guidewire adapter 4 connected by the connection section 4b are freely extendable or retractable. The connection mechanism 9 is provided with a bar-shaped slide section 10 and a receiver section 11. An end of the slide section 10 is connected to the guidewire adapter 4. The receiver section 11 provided in the exterior of the through-hole 7c of the operation section 3 engages with the outer periphery of the slide section 10 and allows the slide section 10 to extend or retract freely.

The slide section 10 is designed so that a distal end section 10a is inserted toward the receiver section 11. In addition, a stopper 12 formed on the side wall section of the distal end section 10a engages with the receiver section 11. The stopper 12 is designed to deform elastically and move inward with respect to the radial direction of the slide section 10 upon inserting the distal end section 10a of the slide section 10 into the receiver section 11 or detaching the stopper 12 from the distal end section 10a of the slide section 10. The stopper 12 prevents the slide section 10 from falling off from the receiver section 11 by limiting the movement of the slide section 10 relative to the receiver section 11 when the slide section 10 is inserted into the receiver section 11 and moves regressively (i.e., proximally relative to a user).

In addition, a click section 13 formed on a part of the side surface of the slide section 10 is capable of engaging with the receiver section 11. The click section 13 projecting outward with respect to the radial direction of the slide section 10 is capable of making elastic deformation inward with respect to the radial direction of the slide section 10.

In addition, the slide section 10 has a proximal end section 10b having a connection section 14 projecting outward with respective to the radial direction of the slide section 10. The cross-sectional shape of a second through-hole 15 formed on the connection section 14 is circular, and the diameter thereof is greater than the diameter of the cylinder section 7. The axial line of the second through-hole 15 is disposed along the axial line of the slide section 10. In this configuration, the axial line of the second through-hole 15 is adjustable to be coaxially with the axial line of the cylinder section 7 when the slide section 10 is connected to the receiver section 11.

Figure 2:
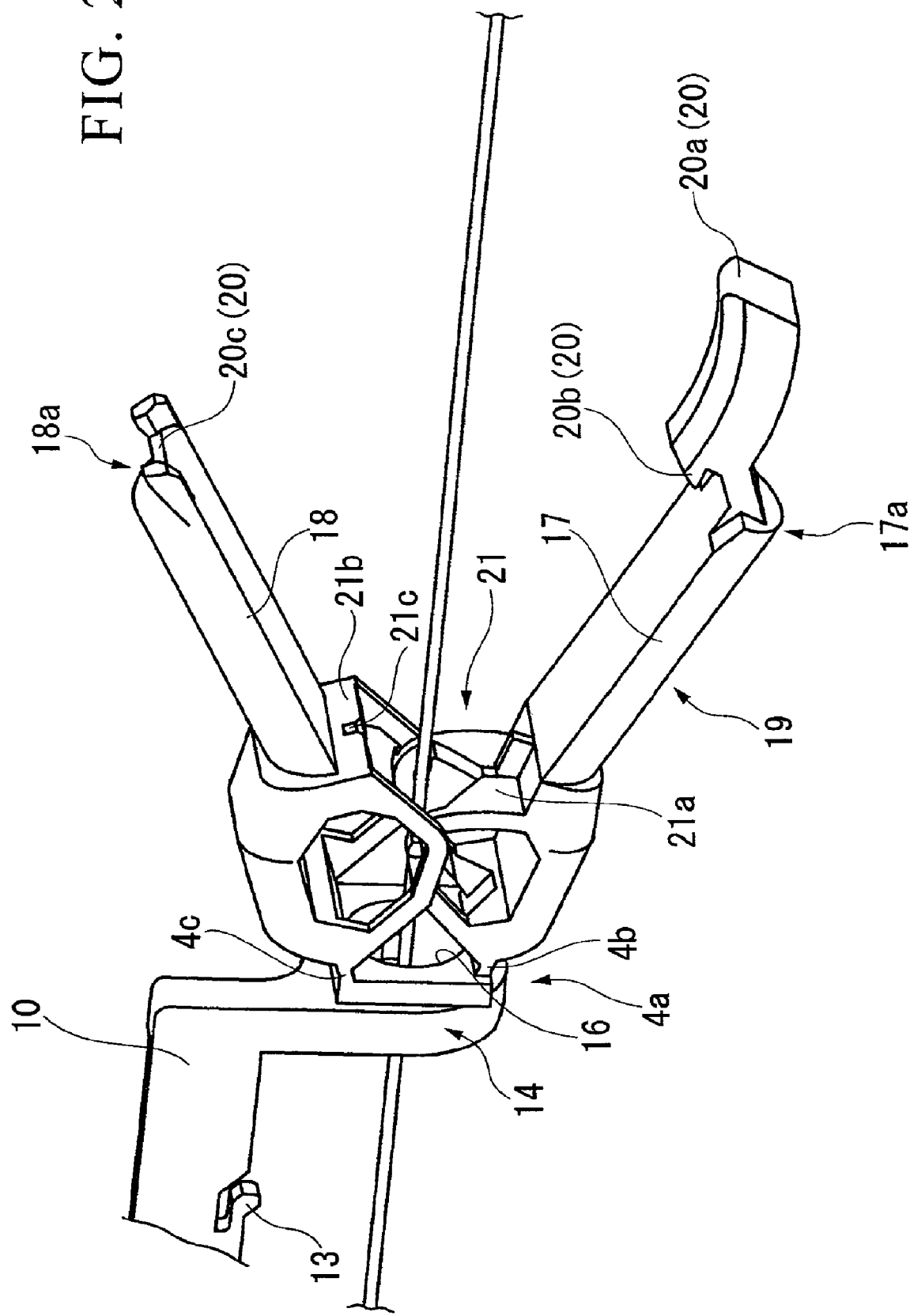
FIG. 2 is an enlarged view of the guidewire adapter of the guidewire catheter.

As shown in FIG. 2, a distal end section 4a of the guidewire adapter 4 inserted into and supported by the connection section 14 is freely rotatable around the axial line. An opening section 16 having a diameter greater than the diameter of the cylinder section 7 is formed on the distal end section 4a of the guidewire adapter 4. In addition, a grip section 19 grasped by an operator includes a pair of proximally extending arms 17 and 18 provided on the distal end section 4a of the guidewire adapter 4.

As shown in FIGS. 2 and 3, the arm 17 and the arm 18 each are formed unitarily with the distal end section 4a. The connection sections 4b that connect the arm 17 to the distal end section 4a and a connection section 4c that connects the arm 18 to the distal end section 4a are formed thinner to have resiliency and flexibility. In addition, a proximal end section 17a of the arm 17 and a proximal end section 18a of the arm 18 are formed to be separable from each other.

The arm 17 and the arm 18 are designed so that the proximal end section 17a and the proximal end section 18a upon being compressed into close proximity provides elastic deformation to the connection section 4b, thereby causing the arm 17 to sway around the connection section 4b and the arm 18 to sway around the connection section 4c. In addition, hooks 20 for fixing the proximate state of the arm 17 and the arm 18 are formed on the proximal end section 17a and the proximal end section 18a.

As shown in FIG. 2, the hooks 20 includes: a projection section 20a further projecting from the proximal end of the proximal end section 17a of the arm 17; an engagement section 20b having a projection; and a mating-engagement section 20c, formed on the proximal end section 18a of the arm 18, that engages with the engagement section 20b.

In addition, as shown in FIG. 2, a pair of clasping sections 21 are formed on a part of the surface of the arm 17 and on a part of the surface of the arm 18 opposing the arm 17. The clasping sections 21 are capable of making contact with the guidewire 5 inserted into the opening section 16. The clasping sections 21 include: a wall section 21a projecting from the arm 17 toward the arm 18 substantially orthogonal with respect to the axis of the arm 17; a wall section 21b projecting from the arm 18 toward the arm 17 substantially orthogonal with respect to the axis of the arm 18; and a recessed section 21c formed on the wall section 21b opposed to the center section of the wall section 21a.

In addition, the wall section 21a has a V-letter shape having the projection height lowering inward with respect to the radial direction of the arm 17. In addition, the size of the recessed section 21c is substantially the same as the diameter of the guidewire 5.

Operation in ERCP using the guidewire catheter 1 having the aforementioned configuration will be explained with reference to FIGS. 3 to 9.

As shown in FIGS. 1 and 3, the guidewire catheter 1 is prepared while an end of the guidewire 5 inserted in orders, into the opening section 16, the cylinder section 7, and the sheath 6 is projected from the distal end of the sheath 6. The length of the guidewire 5 projecting from the sheath 6 is adjusted appropriately.

Figure 4:
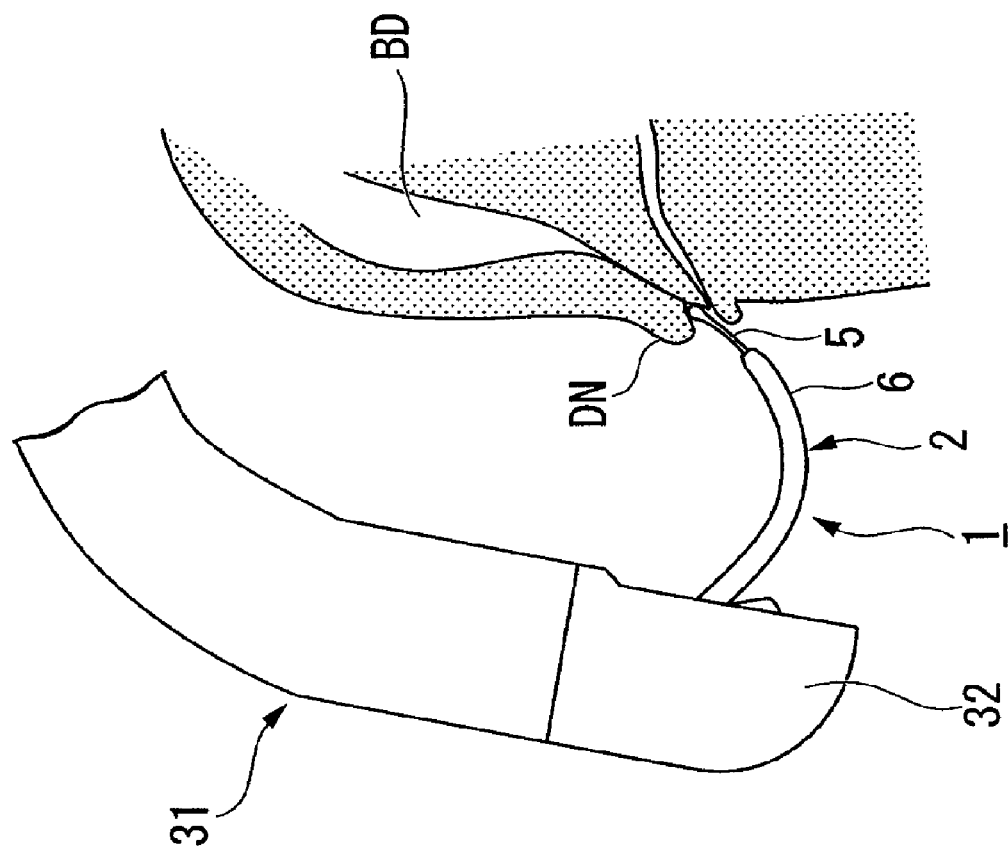
FIG. 4 shows a process of maneuver in the ERCP using the guidewire catheter.

In the beginning, as shown in FIG. 4, an endoscope 31 inserted from a natural orifice of a patent (i.e. a mouth) into the body of the patient is moved to the descending part of duodenum. A side-view endoscope 31 having an observation apparatus on its lateral side can be used in the present embodiment.

The insertion section 2 of the guidewire catheter 1 inserted into a forceps-insertion port of the endoscope 31 disposed proximally in the vicinity of a user passes in an instrument channel to reach a distal end 32 of the endoscope 31. It is preferable that the distal end of the guidewire 5 in this state project from the distal end of the sheath 6 by 2 to 3 millimeters.

Figure 5:
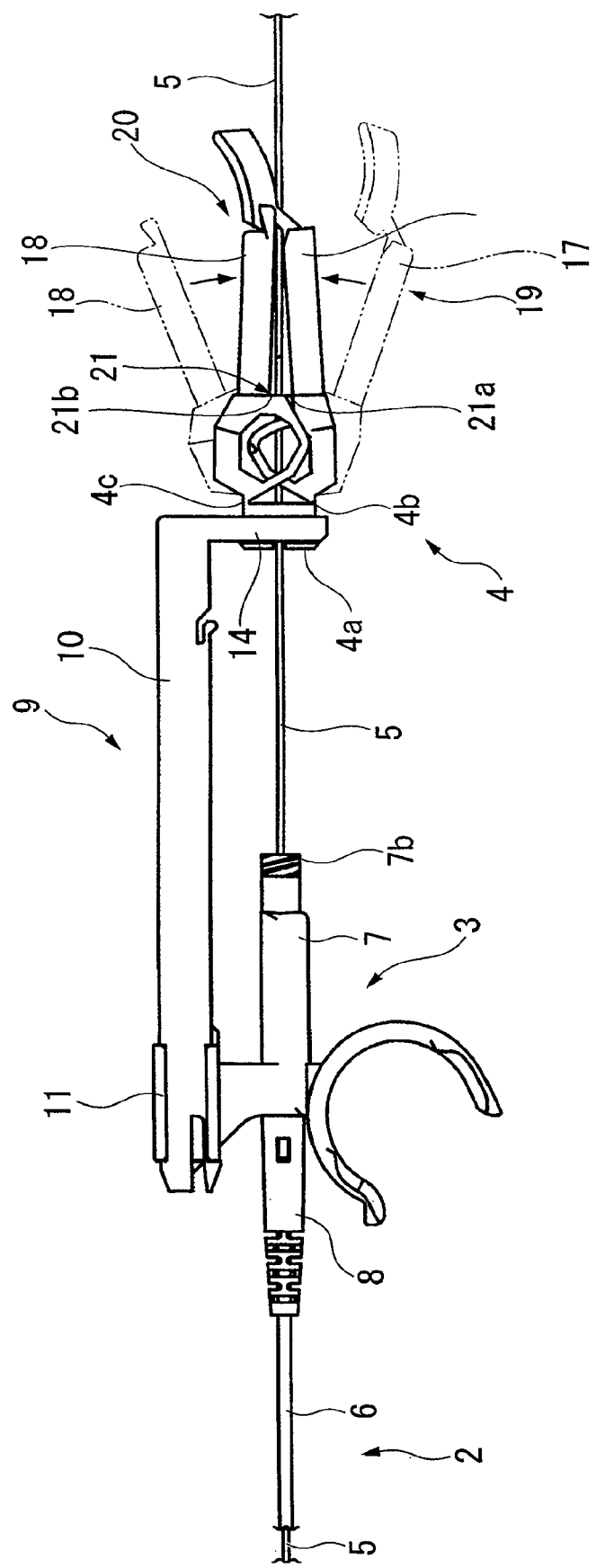
FIG. 5 shows the guidewire catheter in use.

As shown in FIG. 5, the user grasps the grip section 19 disposed proximally relative to the guidewire adapter 4. Subsequently, the pair of arms 17 and 18 opposing each other are compressed to move in proximity with each other. The guidewire 5 is pinched between the wall section 21a and the wall section 21b of the clasping section 21 in this state. Subsequently, the guidewire 5 upon being compressed by the wall section 21a having the V-letter-shape of inclinations as shown in FIG. 2 moves and shifts along the inclination to a central part of the wall section 21a. On the other hand, the guidewire 5 having moved and shifted toward the central part of the recessed section 21c engages with the recessed section 21c of the wall section 21b that opposes the wall section 21a.

Further compressing and moving the arms 17 and 18 cause the hook 20 to fix the proximate state of the arm 17 and the arm 18. The guidewire 5 in this state compressed and fixed by the wall section 21a and the wall section 21b results in being fixed by the grip section 19. This state of the guidewire 5 is designed to be disposed on the axial line of the cylinder section 7 between the cylinder section 7 and the clasping section 21.

As shown in FIG. 6, the guidewire 5 upon being fixed by the hook 20 using the clasping section 21 can be extended, retracted, or rotated with respect to the operation section 3 by extending, retracting, or rotating the grip section 19 with respect to the operation section 3. Moving the grip section 19 distally relative to the operation section 3 causes the connection mechanism 9 to guide the grip section 19, thereby moving the grip section 19 along the axial line of the cylinder section 7 of the operation section 3. This state of guidewire 5 while being fixed to the clasping section 21 and compressed along the axial line of the cylinder section 7 is allowed to make extending movement in the sheath 6 relative to the sheath 6.

Consequently, moving the guidewire 5 distally relative to the sheath 6 results in extending the guidewire 5 relative to the distal end section of the sheath 6.

As shown in FIG. 7, freely extending or retracting movement of the slide section 10 relative to the receiver section 11 is limited by the click section 13 which makes contact with the proximal end section of the receiver section 11. Further compressing the grip section 19 into the operation section 3 while the arms 17 and 18 are fixed by the hook 20 causes the clasping section 21 to make contact with the port 7b. The extending or retracting movement of the inner wall section of the receiver section 11 compressed by the click section 13 in this state is limited.

As shown in FIG. 8, the user extends or retracts the guidewire 5 by extending or retracting the grip section 19 relative to the operation section 3. Subsequently, the user inserts the distal end of the guidewire 5 into the opening section of a nipple DN. In a case of not readily identifying the opening section, a position that enables the insertion of the distal end of the guidewire 5 may be located by extending or retracting the grip section 19 and searching for the opening section of the nipple DN so that the distal end of the guidewire 5 makes contact with the vicinity of the nipple DN.

Upon inserting and passing the distal end of the guidewire 5 through the nipple DN into a bile duct BD, the sheath 6 together with the guidewire 5 are extended from the distal end 32 of the endoscope 31 by moving the operation section 3 distally. Accordingly, the sheath 6 is inserted through the opening section of the nipple DN into the bile duct BD.

Figure 9:
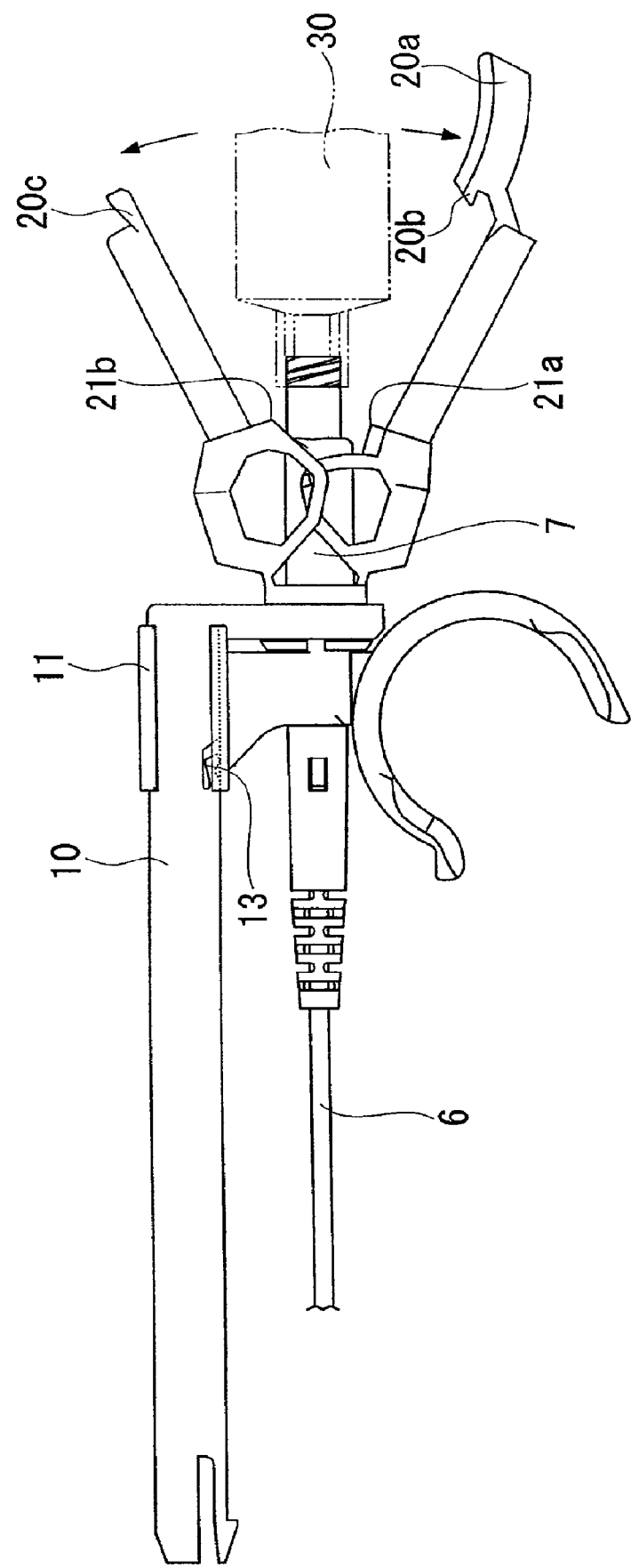
FIG. 9 shows the guidewire catheter in use.

Upon inserting the sheath 6 into the bile duct BD and reaching to an object site, the guidewire 5 is removed from the guidewire catheter 1. FIG. 9 shows the guidewire catheter 1 from which the guidewire 5 has been removed. In the beginning, elastic deformation is applied to the projection section 20a to release the engagement between the engagement section 20b and the mating-engagement section 20c. Subsequently, the elasticity of the connection section 4b connected to the arm 17 and the elasticity of the connection section 4c connected to the arm 18 cause the arm 17 and the arm 18 to move in directions that separate them from each other. This releases the fixed state of the guidewire 5 by the wall section 21a and the wall section 21b, thereby rendering the guidewire 5 freely extendable or retractable. The guidewire 5 projecting from the opening section 16 is retracted proximally by the user. The guidewire 5 can be so removed from the guidewire catheter 1. The distal end of the sheath 6 in this state remains immovable and resides in the bile duct BD.

The grip section 19 upon removing the guidewire 5 is further extended relative to the operation section 3. The slide section 10 in this state is allowed to be inserted farther into the receiver section 11 relative to the position as shown in FIG. 7. The click section 13 elastically deformable in this state is allowed to make extending or retracting movement while compressing the inner wall of the receiver section 11. Friction produced between the click section 13 and the receiver section 11 limits the extension or retraction of this state of the operation section 3 and the guidewire adapter 4.

On the other hand, if the guidewire adapter 4 is compressed fully into the operation section 3, the cylinder section 7 of the operation section 3 is allowed to pass through the opening section 16. The user can connect a syringe 30, filled with a contrast agent, to this state of the port 7b projecting proximally toward the grip section 19. The distal end of the syringe 30 is brought into close contact with the port 7b by compressing the syringe 30 to the port 7b and rotating the syringe 30 around the axial line of the port 7b since the distal end of the syringe 30 has a leur lock structure that conforms to the port 7b.

The contrast agent supplied from the syringe 30 through the port 7b passes in order, through the cylinder section 7, the sheath 6, and the distal end of the sheath 6, and is injected into the bile duct BD. The user captures roentgenologic contrast radiographic images of the bile duct BD filled with the contrast agent thereinside. Upon obtaining the roentgenologic images, the guidewire catheter 1 is removed to finish the treatment.

A conventional guidewire catheter has used an apparatus commonly called a torque device that is an operation assistant instrument for assisting operation including the extension or the retraction of a guidewire inserted through a sheath by fixing the outer periphery surface of the guidewire. However, the important point to note is that the insertion of guidewire into the sheath with the torque device necessitates the guidewire to be inserted straight into a proximal opening of the sheath in order to prevent the guidewire from bending. Another problem was that, leaving a hand from the torque device during a process of treatment might sometimes cause the guidewire to hang over by the self weight thereof, thereby hindering the maneuver.

Japanese Unexamined Patent Application, First Publication No. 2003-79741 discloses another guidewire adapter that uses a freely slidable elongated tubular guide member inserted through a lumen of a through-hole of a tubular member that allows a guidewire to pass therethrough. However, increasing a stroke length (e.g. 7 cm) for facilitating the extension or retraction of a guidewire in this configuration necessitates the lumen of the tubular member to have a length that accommodates the full stroke length of the slidable member. Therefore, adding up the lengths of the receiver and the slide section obtains at least a doubled stroke length which will be problematic because it is too long in view of operability. (In case of a stroke length of 7 cm, the sum of lengths of the receiver and the slide section is at least 14 cm.)

The present application has an advantageous operability because the sum of the lengths of the receiver and the slide section can be substantially the same as the stroke length, and the guidewire adapter can be compact when it is attached to the operation section since the slide member is disposed in line with and in the exterior of a through-hole which allows a guidewire to pass therethrough.

The guidewire catheter 1 according to the present embodiment is designed so that the connection mechanism 9 connects the operation section 3 to the guidewire adapter 4, and so that the guidewire adapter 4 extends or retracts along the axial line of the cylinder section 7. This allows the guidewire 5 gripped by the guidewire adapter 4 to be inserted into the sheath 6 to be free from bending.

A second embodiment of the present invention will be explained next with reference to FIGS. 10 to 17. A guidewire catheter of the present embodiment is different from the aforementioned guidewire catheter 1 based on the configuration of the guidewire adapter.

It should be noted that configurations that are similar to those of the previously explained first embodiment will be assigned the same numeric symbol and redundant explanation thereof will be omitted.

Figure 10:
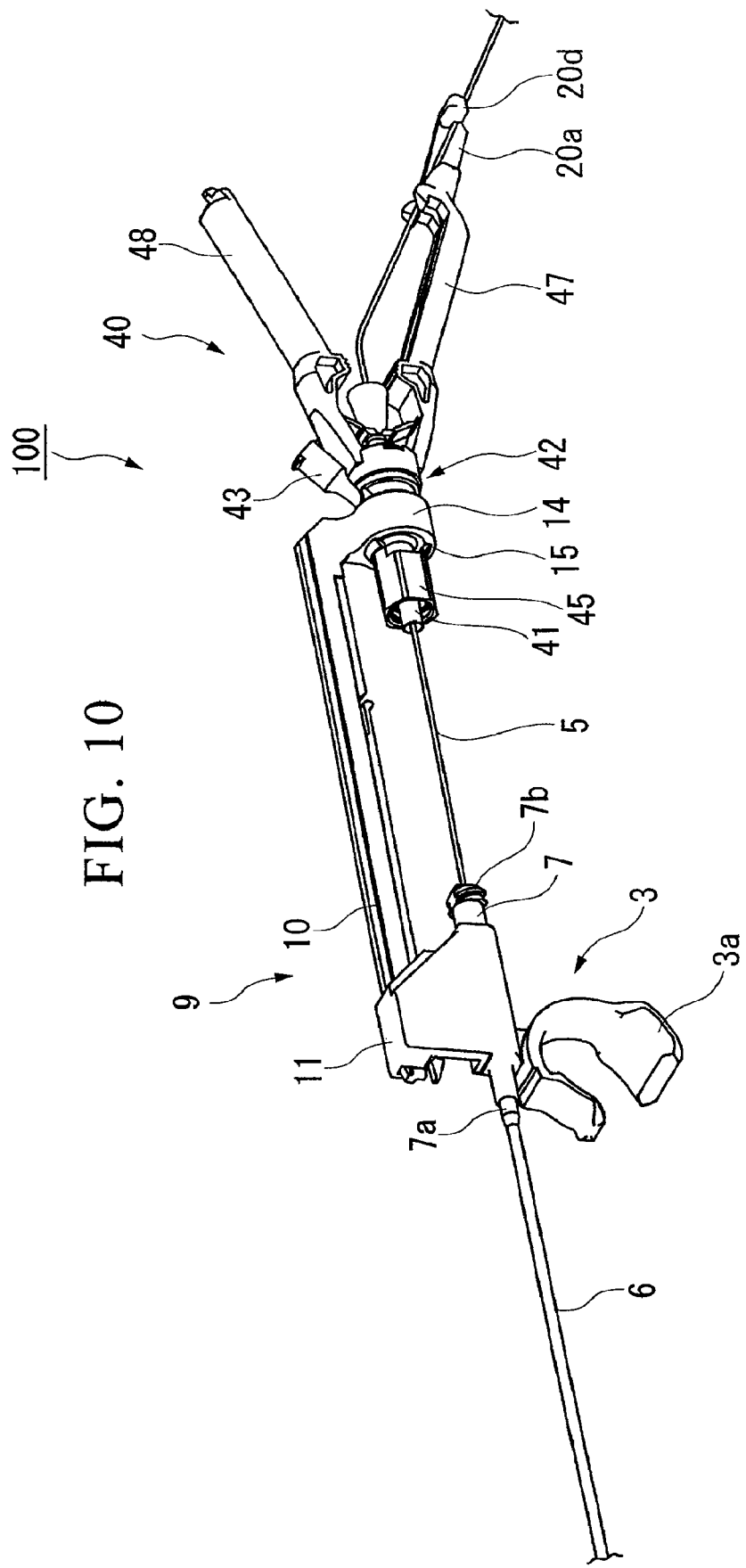
FIG. 10 shows a guidewire catheter according to a second embodiment of the present invention.
Figure 11:
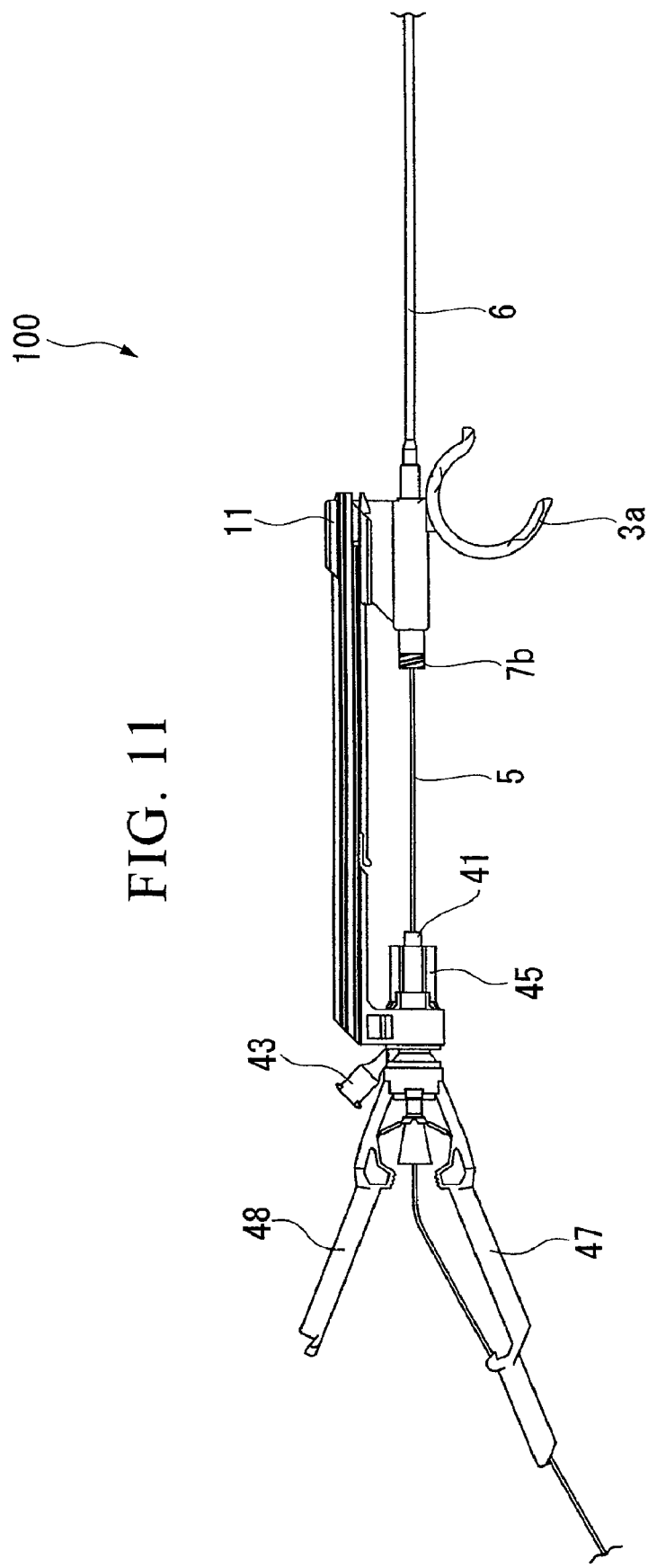
FIG. 11 shows a guidewire catheter according to the second embodiment of the present invention.

As shown in FIGS. 10 and 11, a guidewire catheter 100 according to the second embodiment is configured to include a guidewire adapter 40 in place of the guidewire adapter 4 according to the first embodiment.

The configuration of the guidewire adapter 40 is different from that of the guidewire adapter 4 according to the first embodiment because the guidewire adapter 40 is provided with: a cylindrical main unit 41 that allows the guidewire 5 to pass therethrough and is capable of communicating with the lumen of the sheath 6; a seal mechanism 42, connected to the proximal end section of the main unit 41, that allows the guidewire 5 to pass therethrough and seals the proximal opening of the main unit 41; a sideport 43 that communicates with the lumen between the sheath 6 and the seal mechanism 42; and a pair of arms 47 and 48, connected to the seal mechanism 42 and opposed in the radial direction in the exterior of the of the guidewire, that grasp the guidewire 5

The distal end of the main unit 41 is inserted into the second through-hole 15 of the connection section 14, and the main unit 41 is locked in this state. In addition, the main unit 41 is freely rotatable around the axial line of the second through-hole 15 relative to the connection section 14. In addition, the axial line of the cylinder section 7 is configured to be substantially coaxial with the axial line of the main unit 41 when the main unit 41, the connection mechanism 9, and the operation section 3 are assembled together. In addition, a leur lock section 45, formed on the distal end section of the main unit 41, is connected with the port 7b of the cylinder section 7. In this configuration, the leur lock mechanism provides waterproof connection by connecting the cylinder section 7 and the main unit 41 seamlessly.

Figure 12:
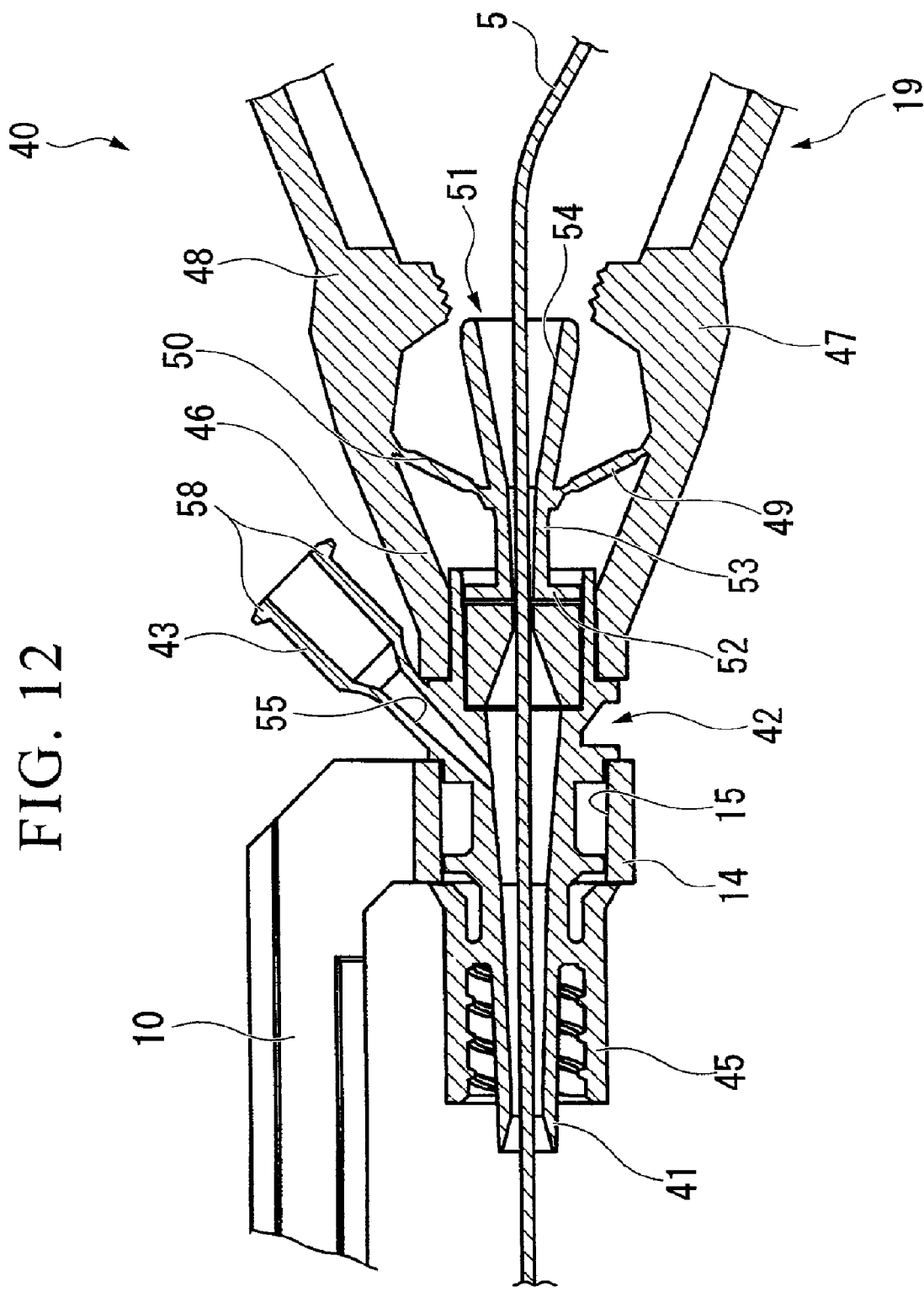
FIG. 12 is an enlarged cross-sectional view of the guidewire adapter of the guidewire catheter.

As shown in FIG. 12, the seal mechanism 42 is provided with a seal member 46 and a pusher 51. The seal member 46 is made from an elastic member provided to the proximal end of the main unit 41. The pusher 51 has link mechanisms 49 and 50, disposed proximal relative to the seal member 46, that are connected to the pair of arms 47 and 48 respectively.

The distal end of the cylindrical seal member 46 made of an elastic material, for example, rubber is inserted into the main unit 41. In addition, the inner wall of the seal member 46 has a substantial conical surface that inclines outward from the proximal end to the distal end thereof with respect to the radial direction. In addition, the guidewire 5 inserted through the seal member 46 is freely extendable or retractable in this configuration.

The pusher 51 is disposed coaxially with the proximal end of the seal member 46. In addition, the pusher 51 includes: a pusher plate 52, formed in the proximal end of the seal member 46, that is capable of making contact with the proximal end of the seal member 46; a pusher main unit section 53 having a cylindrical shape in the vicinity of the proximal end of the pusher plate 52; and link mechanisms 49 and 50 that connect the arms 47 and 48 respectively to the outer periphery surface of the pusher main unit section 53. A through-hole 54 formed through the pusher plate 52 and the pusher main unit section 53 coaxially with the axial line of the main unit 41 allows the guidewire 5 to freely extend or retract therethrough.

In addition, the through-hole 54 formed in the pusher main unit section 53 has a substantial conical shape that increases the radial direction outwardly toward the proximal end thereof. That is, the diameter of the opening formed on the proximal end section of the pusher main unit section 53 is greater than the diameter of the opening formed on the distal end section of the pusher main unit section 53. Therefore, in this configuration, an end of the guidewire 5 inserted into the proximal end section of the pusher main unit section 53 is guided through the through-hole 54 and inserted into the seal member 46 via a pusher plate 52.

In addition, the link mechanisms 49 and 50 are sheet plates that are formed with the arms 47 and 48 and the pusher main unit section 53 unitarily so that sections that connect the arms 47 and 48 to the pusher main unit section 53 are swayable respectively.

As shown in FIG. 12, a through-hole 55 formed in the sideport 43 reduces its inner diameter toward the distal end of the main unit 41 and communicates with the inner space in the main unit. In addition, a commonly known leur lock mechanism is applicable to an outer periphery section 58 formed on the proximal opening of the sideport 43. The sideport 43 is designed to allow a section of a liquid-supply instrument including a syringe or the like that is adaptable to the leur lock mechanism to be connected thereto directly or via an appropriate adapter.

Figure 13:
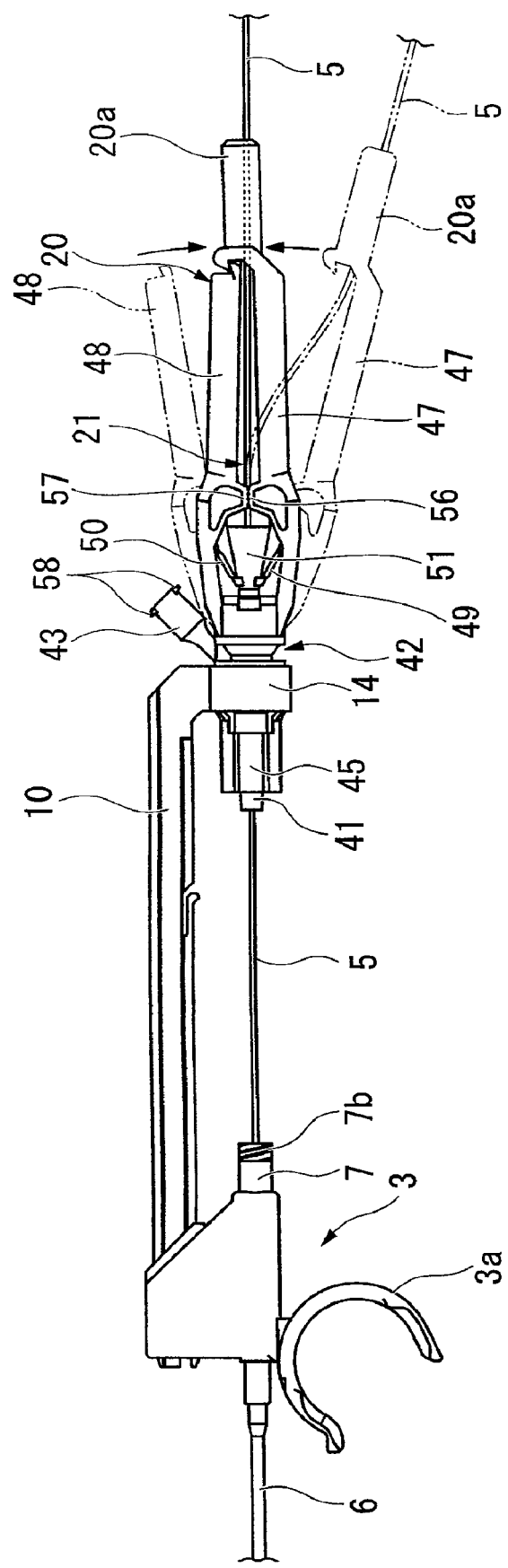
FIG. 13 shows the movement of the guidewire adapter of the guidewire catheter.

As shown in FIG. 13, the arm 47 and the arm 48 of the present embodiment having the hooks 20 are similar to the first embodiment. A lock section 20d that locks the guidewire 5 is formed on the projection section 20a in the present embodiment (see FIG. 10). In addition, the clasping section 21 has a pair of opposing corrugated surfaces 56 and 57 in place of the wall sections 21a and 21b. In this configuration, the corrugated surfaces 56 and 57 prevent the guidewire 5 from slipping.

Operation of the guidewire catheter 100 having the aforementioned configuration and used in the ERCP will be explained with reference to FIGS. 12 to 17. Operation in ERCP using the guidewire catheter 100 having the aforementioned configuration will be explained with reference to FIGS. 12 to 17.

FIG. 12 shows the guidewire catheter 100 prepared by inserting the guidewire 5 into the proximal end of the pusher main unit section 53 and through the seal member 46 and the main unit 41, and further through the cylinder section 7 and the sheath 6 as shown in FIG. 13.

Figure 14:
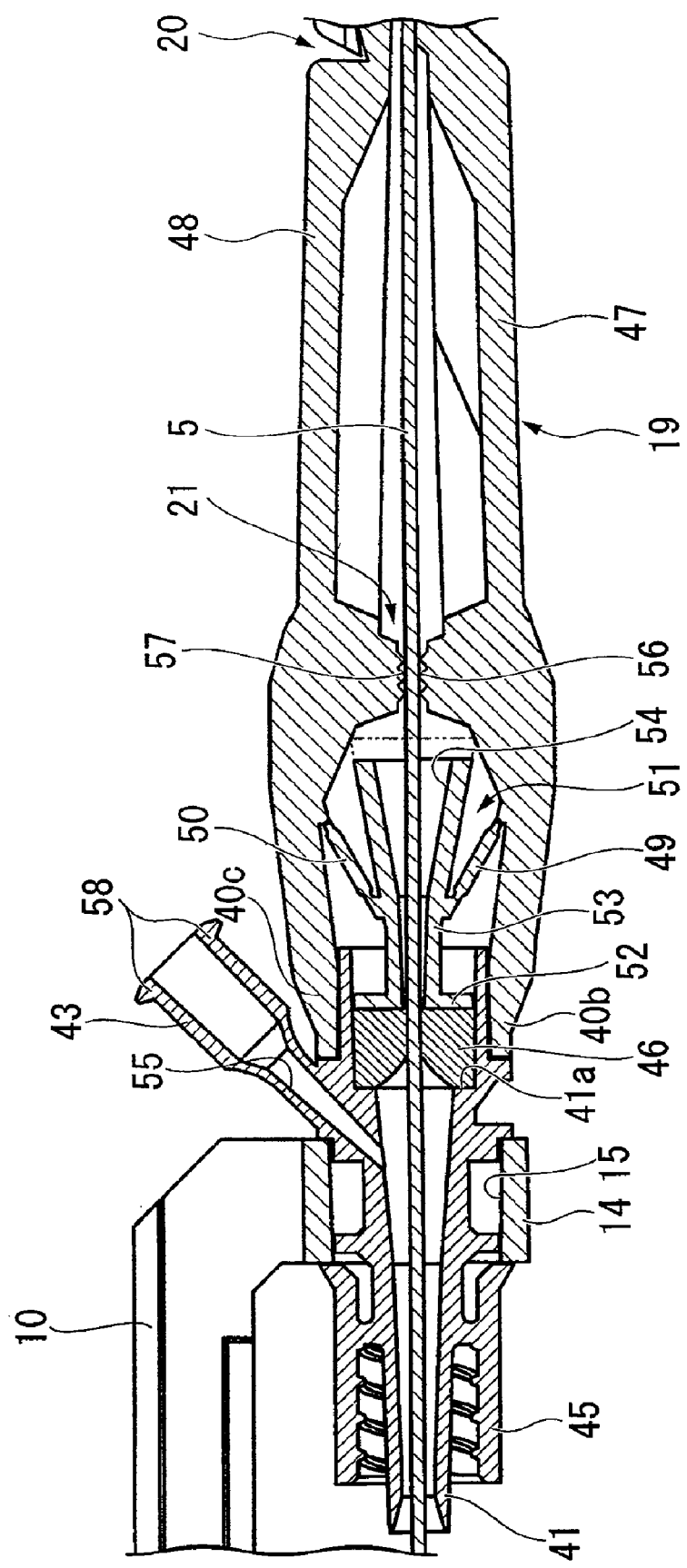
FIG. 14 shows the movement of the guidewire adapter of the guidewire catheter.

Similarly to the first embodiment, the user extends the endoscope 31 to the descending part of duodenum and adjusts the visual field to include the nipple DN. Subsequently, when the user grips the arms 47 and 48 of the guidewire adapter 40, the opposing arms 47 and 48 are compressed to come close to each other As shown in FIG. 14, the outer periphery surface of the guidewire 5 is grasped by the corrugated surfaces 56 and 57 of the clasping section 21. When the arms 47 and 48 are moved further, the hooks 20 fix the proximate state of arms 47 and 48. The guidewire 5 in this state is fixed by the clasping section 21.

On the other hand, when the arm 47 and the arm 48 move in the directions that cause them to come close to each other, the link mechanisms 49 and 50 connected to the arms 47 and 48 respectively are compressed by swayable movement around connecting sections 40b and 40c. The connecting section 40b connects the arm 47 to the guidewire adapter 40, and the connecting section 40c connects the arm 48 to the guidewire adapter 40.

Consequently, the compressing forces transferred from the arm 47 and the arm 48 are converted to move the pusher main unit section 53 along the axial line thereof. This results in causing the pusher main unit section 53 to compress the seal member 46 via the pusher plate 52. The seal member 46 upon being compressed by the pusher plate 52 is elastically deformed and compressed since the seal member 46 is inserted into the main unit 41.

Simultaneously, in this configuration, the distal end section of the seal member 46 makes close contact with a rim section 41a formed on the proximal opening of the main unit, and the through-hole formed along the axial line of the seal member 46 contracts to make close contact with the outer periphery section of the guidewire 5. Accordingly, the proximate and fixed state of arms 47 and 48 causes the main unit 41, the guidewire 5, and the seal member 46 to make close contact with each other, thereby providing waterproof state therebetween.

Similarly to the first embodiment, the user grasping the grip section 19 inserts the distal end of the guidewire 5 into the opening section of the nipple DN by extending, retracting, or rotating the guidewire 5. Upon inserting the distal end of the guidewire 5 into the nipple DN, the distal end of the sheath 6 is inserted into the bile duct BD along the guidewire 5 via the opening section of the nipple DN.

Figure 15:
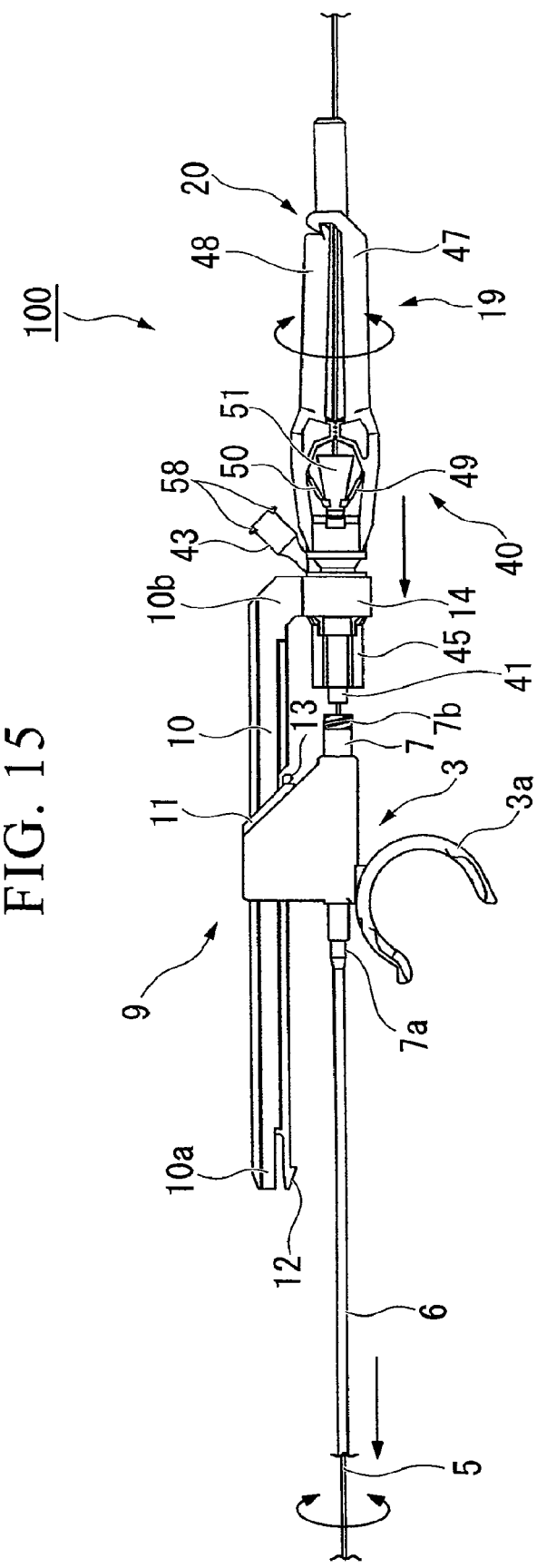
FIG. 15 shows the movement of the guidewire catheter in use.

As shown in FIG. 15, the connection mechanism 9 is configured to move the guidewire adapter 40 linearly along the axial line of the cylinder section 7 when the grip section 19 is extended or retracted. In this configuration, inadvertent connection between the port 7b the leur lock section 45 is prevented when the grip section 19 is moved or rotated since the port 7b of the operation section 3 is configured not to make contact with the leur lock section 45 of the guidewire adapter 40 at a position where the click section 13 formed on the slide section 10 makes contact with the receiver section 11.

Figure 16:
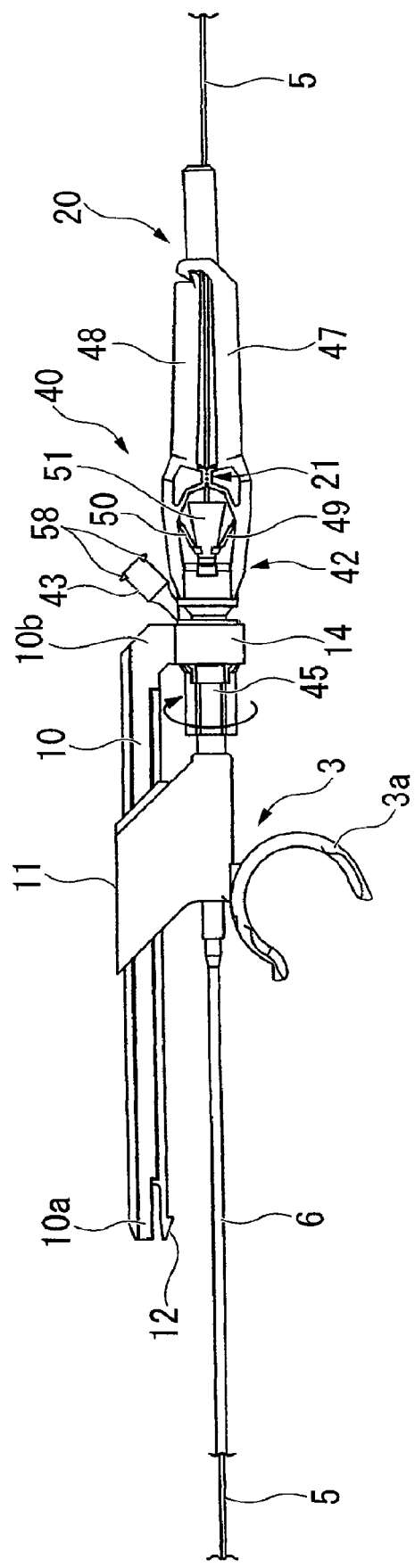
FIG. 16 shows the movement of the guidewire catheter in use.
Figure 17:
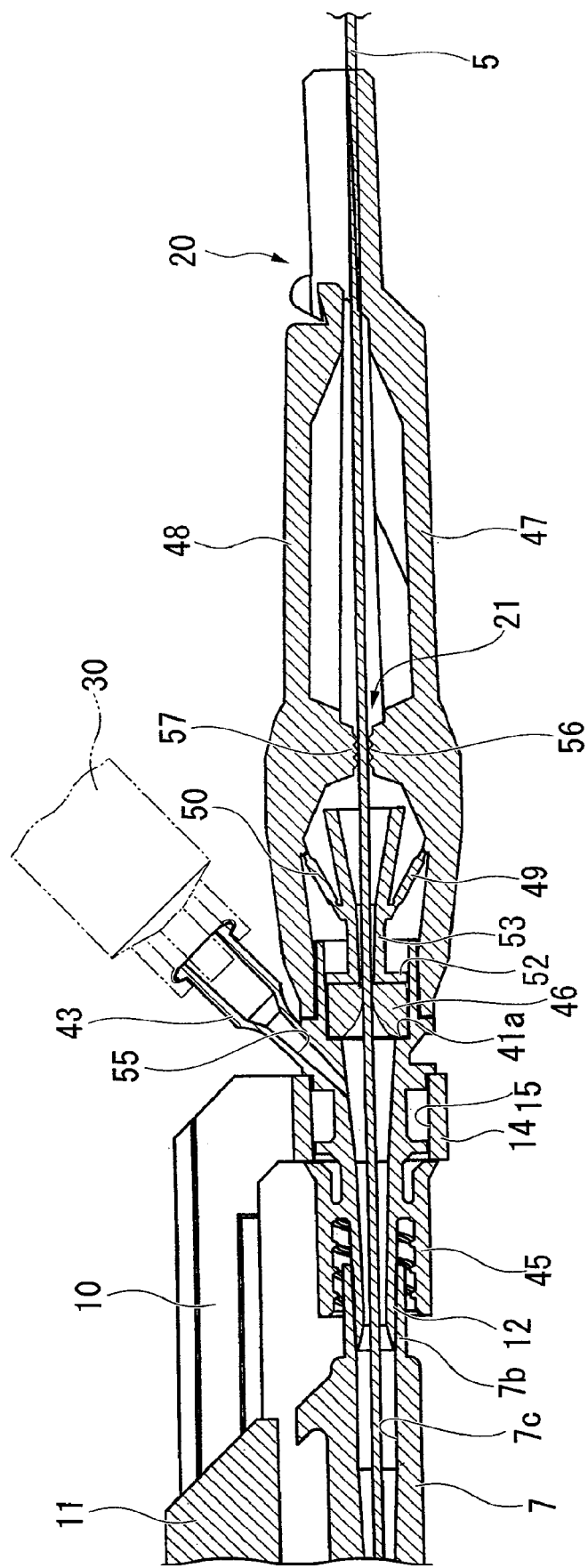
FIG. 17 is a fragmentary cross-sectional view showing the movement of the guidewire adapter of the guidewire catheter in use.

As shown in FIG. 16, the user fastens the leur lock section 45 of the guidewire adapter 40 into the port 7b of the cylinder section 7 of the operation section 3 while further compressing the slide section 10 toward the operation section 3. This provides waterproof connection between the port 7b and the leur lock section 45. In addition, as shown in FIG. 17, the user attaches the syringe 30 filled with the contrast agent to the sideport 43. The contrast agent is supplied from the syringe 30 into the main unit 41 via the through-hole 55 of the sideport 43.

As previously explained, the contrast agent moves toward the distal end of the main unit since the proximal end of the main unit 41 maintains the waterproof condition while the arms 47 and 48 are fixed by the hooks 20. The contrast agent passing through a gap between the guidewire 5, the cylinder section 7, and the sheath 6 and supplied to the distal end of the sheath 6 is ejected from the distal end of the sheath 6 into the bile duct BD. The user captures roentgenologic contrast radiographic images of the bile duct BD filled with the contrast agent thereinside. Upon obtaining the roentgenologic images, the guidewire 5 and the guidewire catheter 100 are removed to finish the treatment.

Operations using a conventional guidewire catheter were complex because an operation for grasping a guidewire was separate from an operation for maintaining waterproof condition in a space between the guidewire and a main unit in the vicinity of a user's hand from which a contrast agent is supplied.

In the guidewire catheter 100 according to the present embodiment, a gripping movement conducted to the arms 47 and 48 of the guidewire adapter 40 simultaneously causes an operation for fixing the guidewire 5 and an operation for maintaining the waterproof state between the guidewire 5 and the main unit 41 in the vicinity of the user's hand, thereby facilitating the operations.

A third embodiment of the present invention will be explained next with reference to FIGS. 18 to 20.

Figure 18:
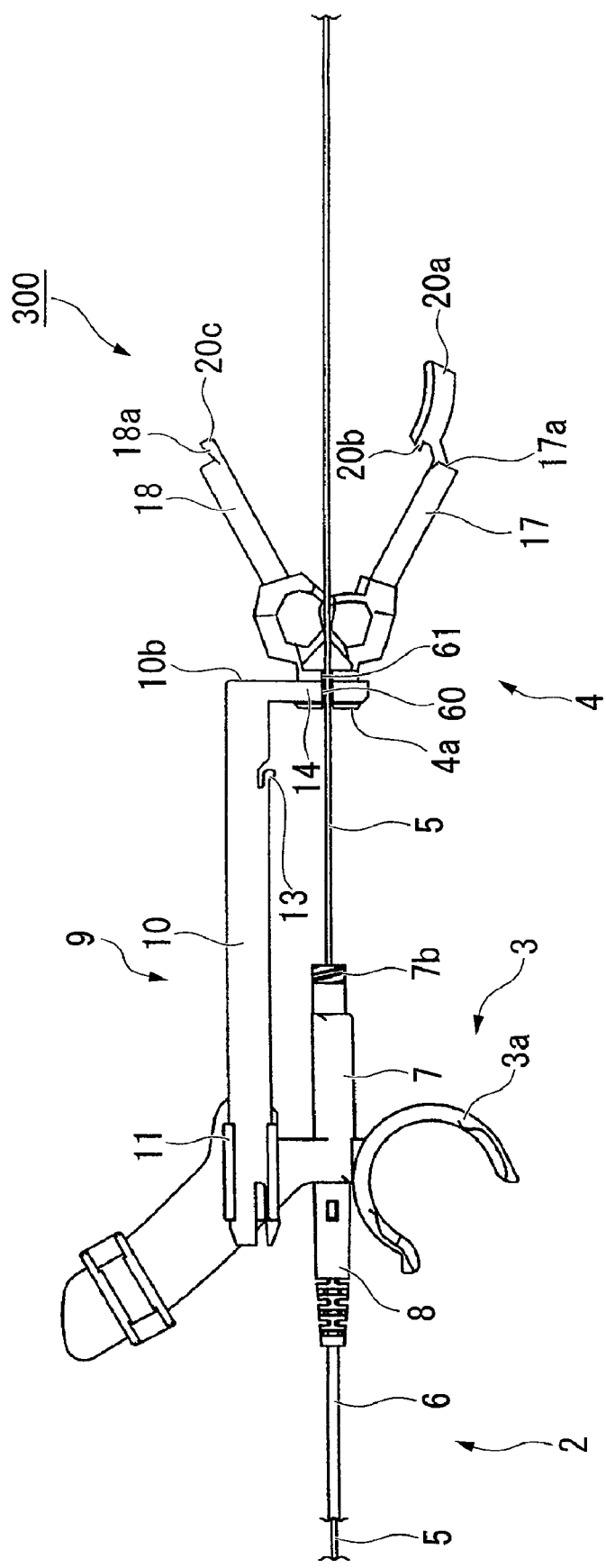
FIG. 18 shows a the guidewire catheter according to a third embodiment of the present invention.

As shown in FIG. 18, a guidewire catheter 300 according to the present embodiment has a configuration different from that of the first embodiment because incised sections 60 and 61 are formed on the connection section 14 of the connection mechanism 9 and the distal end section 4a of the guidewire adapter 4 respectively.

Similarly, the connection section 14 engages with the distal end section 4a so that the two components are freely rotatable with each other. Therefore, in this configuration, the positions of the incised sections 60 and 61 are variable between a connecting state or a disconnecting state of the connection section 14 relative to the distal end section 4a.

Figure 19:
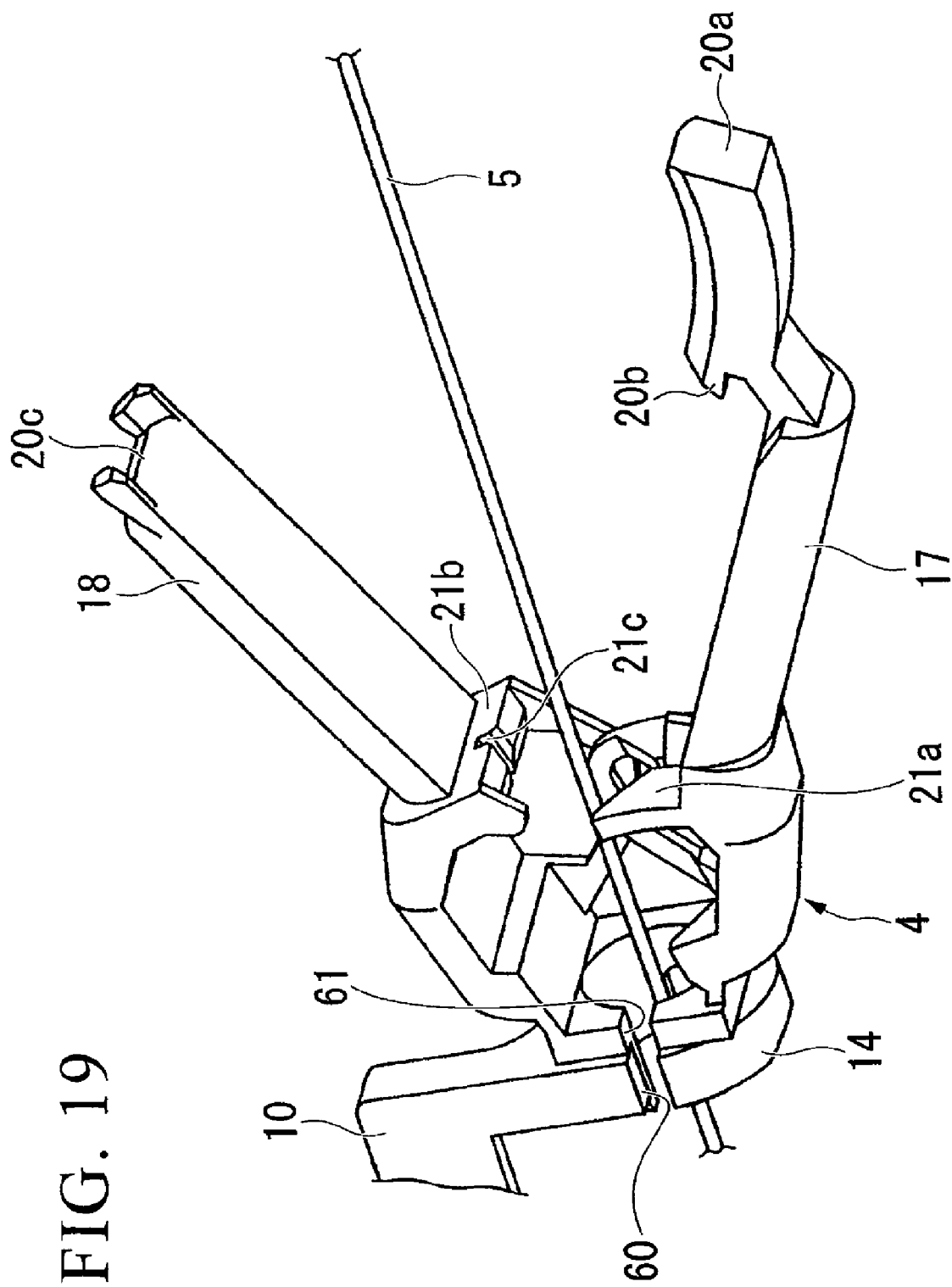
FIG. 19 shows the movement of the guidewire catheter in use as shown in FIG. 18.
Figure 20:
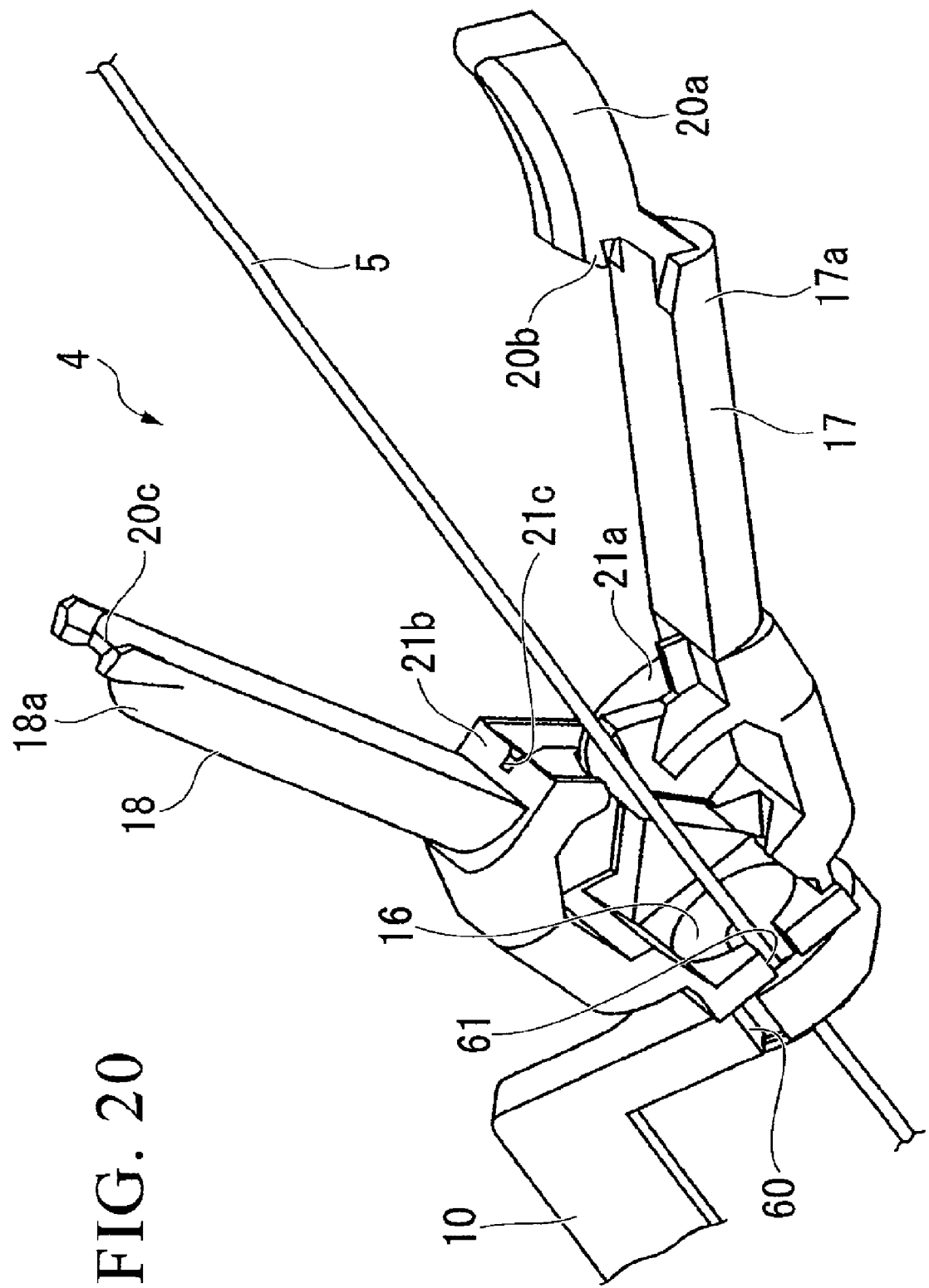
FIG. 20 shows the movement of the guidewire catheter in use as shown in FIG. 18.

As shown in FIG. 19, when the incised sections 60 and 61 coincide with each other, a space communicating to the opening section 16 is produced. On the other hand, the space communicating to the opening section 16 is not produced when the incised sections 60 and 61 do not coincide as shown in FIG. 20.

In this configuration of the guidewire catheter 300, in the beginning, the guidewire adapter 4 is rotated around the axial line in the circumferential direction relative to the connection section 14 to coincide the incised sections 60 and 61. Subsequently, the guidewire 5 is inserted into the opening section 16 via the incised sections 60 and 61.

In the present embodiment, the insertion of the guidewire catheter 300 into the guidewire 5 can be facilitated since the guidewire 5 can be inserted into the lateral side of the opening section 16. In addition, the guidewire 5 is maintained in the opening section 16 unless the position of the incised section 60 coincides with the position of the incised section 61 in the circumferential direction.

Figure 21:
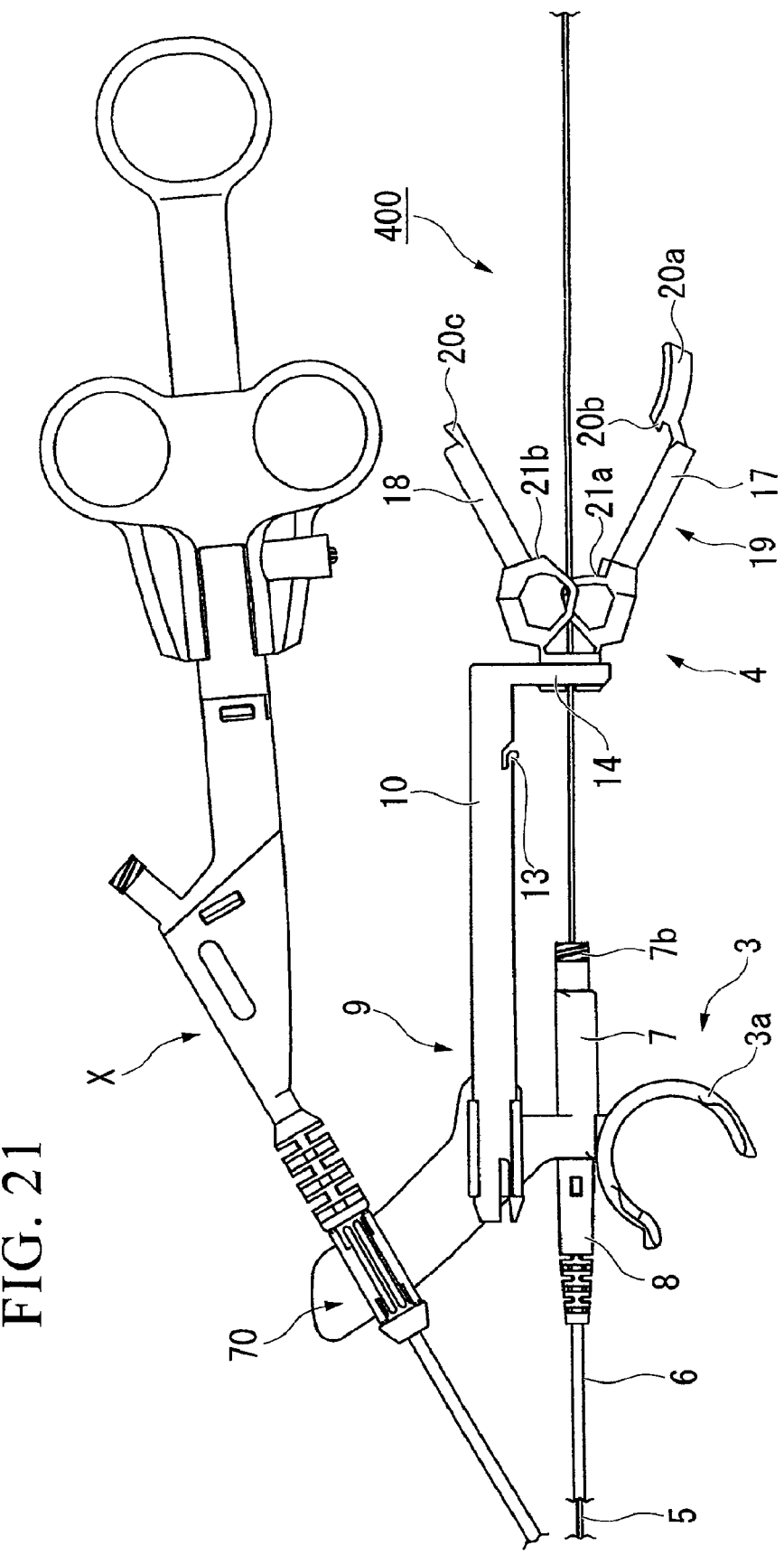
FIG. 21 shows the guidewire catheter according to a fourth embodiment of the present invention.

A fourth embodiment of the present invention will be explained next with reference to FIG. 21.

A guidewire catheter 400 according to the present embodiment is supposed to be used with various endoscopically usable instruments. As shown in FIG. 21, the guidewire catheter 400 has a configuration different from that of the first embodiment because the guidewire catheter 400 is provided with a holder section 70 for fixing and holding an instrument X.

A conceivable example for the instrument X may be a high-frequency knife or the like for incising the nipple DN. This case of the sheath 6 can be used with one of lumens of the high-frequency knife into which the sheath 6 is inserted, of the sheath 6 can be disposed along the tube of the high-frequency knife.

This configuration reduces complexity in operations using the guidewire catheter together with the instrument X since the guidewire catheter 400 and the instrument X can be used as a single component.

Although the present invention has been described with respect to its preferred embodiments, the present invention is not limited to the embodiments described above. The configuration of the present invention allows for addition, omission, substitution and further modification without departing from the spirit and scope of the present invention.

For example, as shown in a chain double-dashed line in FIG. 14, the proximal end section of the pusher 51 can be extended to form a cam structure that makes contact with the arm 47 and the arm 48 and compresses the pusher main unit section 53 by means of the arm 47 and the arm 48.

In addition, the configuration of the present invention is not limited to the embodiment using the connection mechanism 9 including the receiver section 11 provided on the operation section 3 and the slide section 10 having the connection section 14. A configuration including a bar-shaped slide section provided to the operation section 3 and a receiver having the connection section 14 can achieve the same effect as that of the present invention.

Figure 22:
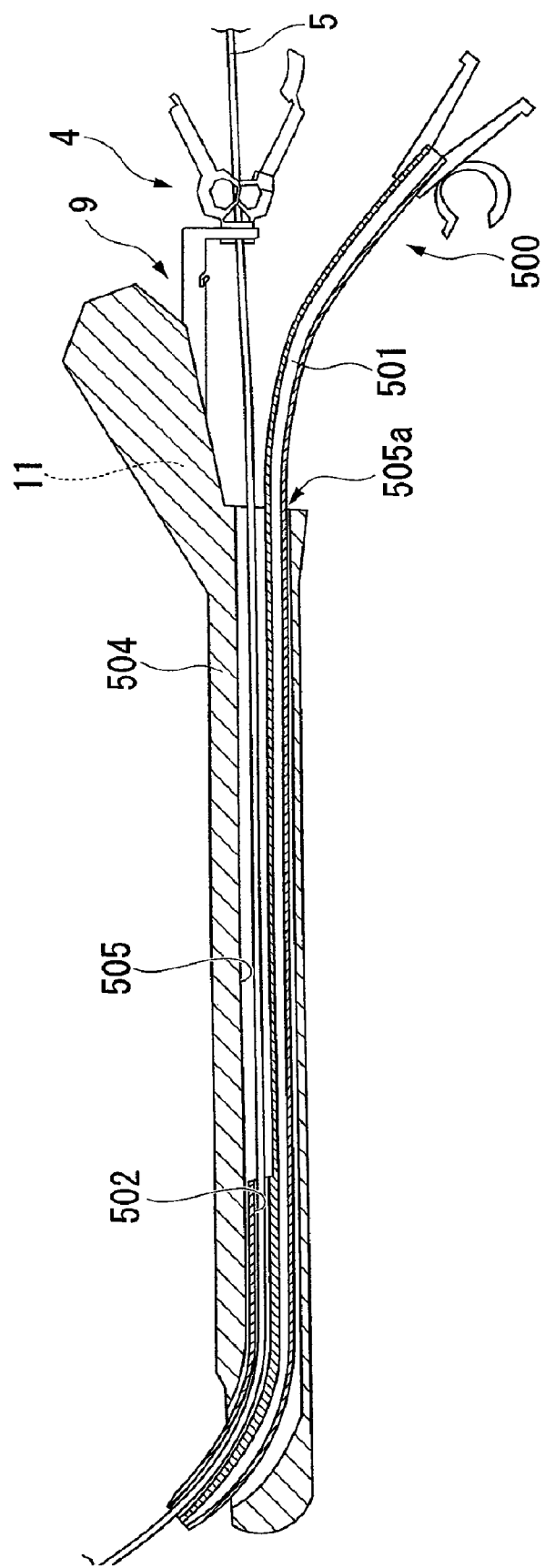
FIG. 22 shows a modified example of the guidewire catheter according to the present invention.
Figure 23:
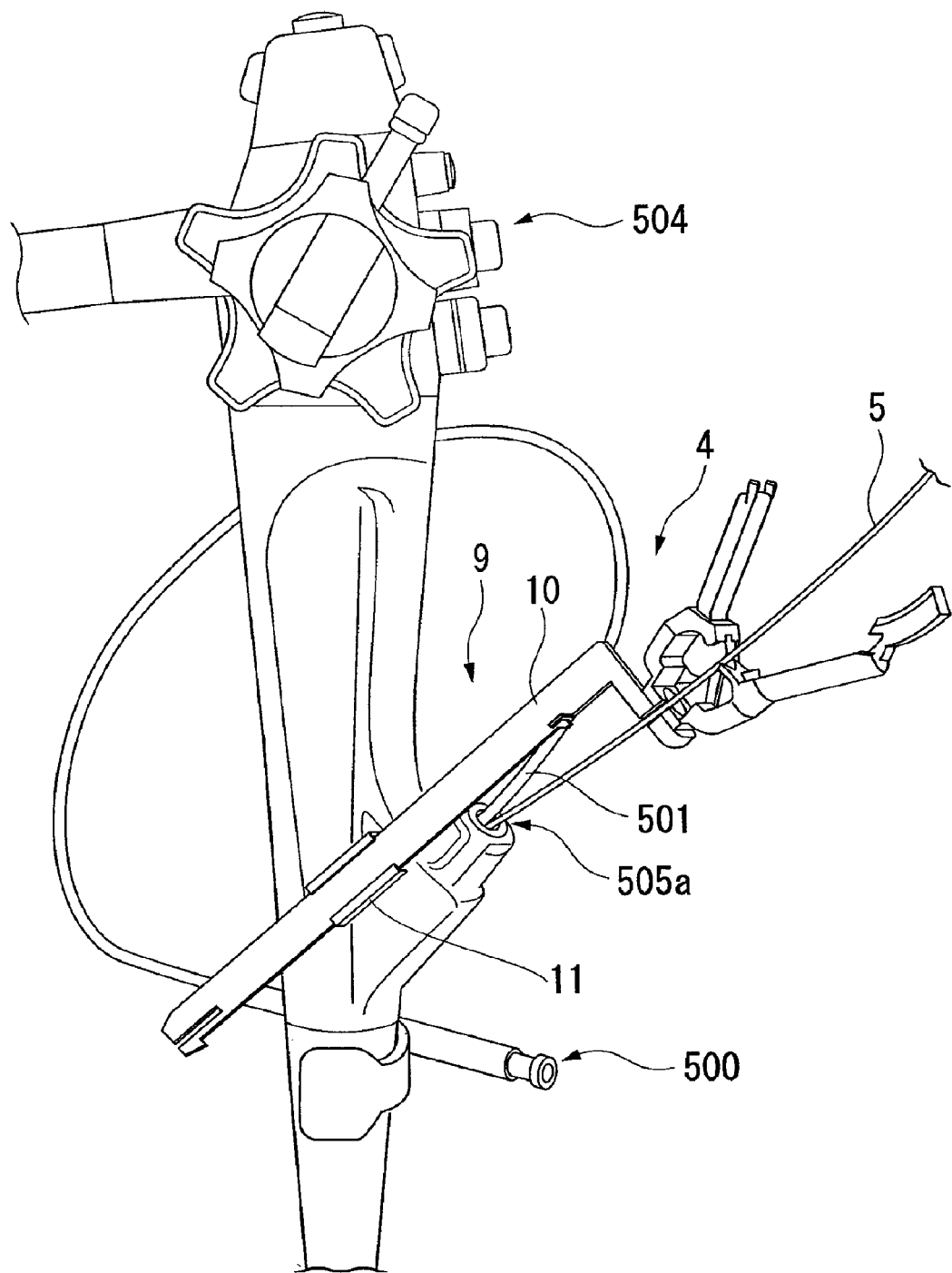
FIG. 23 shows the movement of the guidewire catheter in use as shown in FIG. 22.

In addition, the configuration of the present invention is not limited to the embodiment using the guidewire adapter 4 connected to the operation section 3 via the connection mechanism 9. FIGS. 22 and 23 show a configuration using a catheter 500 having a lumen 501 used for taking contrast radiographic images and a guidewire lumen 502 having an opening provided in the middle of the catheter 500 in which the receiver section 11 is fixed in the vicinity of the exterior of an insertion port 505a of an instrument channel 505 which allows the insertion of the catheter 500 into the endoscope 504. Moving the guidewire adapter 4, which is extendable or retractable relative to the endoscope 504, while maintaining the catheter 500 immovable relative to the endoscope 504 allows the guidewire 5 to extend or retract relative to the catheter 500. This can also prevent the section of the guidewire 5 exposed from the insertion port 505a of the endoscope 504 from bending when the guidewire 5 is extended, retracted, or rotated. In addition, the guidewire adapter 4 does not necessitate the operation section of the endoscope 504 that is large in size since the receiver section 11 is provided in the exterior of the instrument channel 505 of the endoscope 504.

In addition, the configuration of the present invention is not limited to the second embodiment adopting the sideport 43 communicating to the space in the main unit 41, and a configuration adopting the sideport 43 disposed to communicate with the space from the outer periphery surface of the cylinder section 7 can achieve the same effect as that of the present invention.

The present invention is not limited to the above descriptions but is limited only by the appended claims.

What is claimed is:

1. A guidewire catheter comprising:
   a sheath for passing a guidewire therethrough;
   an operation section connected to an end of the sheath and having a through-hole for passing the guidewire therethrough; and
   a guidewire adapter connected to the operation section and capable of freely extending or retracting relative to the operation section along an axial line of the through-hole, the guidewire adapter configured to mechanically grasp the outer surface of the guidewire projecting from the through-hole, and the guidewire adapter being capable of guiding and moving the guidewire relative to the operation section in an axial direction and a circumferential direction of the through-hole, wherein
   the sheath, the operation section, and the guidewire adapter are arranged on an axial line of the guidewire, and the guidewire is configured to be inserted through an entire length of the sheath, the operation section, and the guidewire adapter.

2. A guidewire catheter according to claim 1, further comprising:
   a bar-shaped slide section formed on one of the operation section and the guidewire adapter in the exterior of the through-hole, the slide section being disposed along a line which is parallel with the axial line of the through-hole; and
   a receiver formed on the other one of the operation section and the guidewire adapter and being capable of moving and supporting the freely extendable or retractable slide section.

3. A guidewire catheter according to claim 1, further comprising:
   a connection section having a second through-hole formed coaxially with the axial line of the through-hole; and
   a grip section, engaged with the second through-hole, for grasping an outer periphery surface of the guidewire, and the grip section being freely rotatable around the axial line of the second through-hole.

4. A guidewire catheter according to claim 2, wherein
   the bar-shaped slide section has a click section, and
   the receiver is configured to engage with the click section and grasp the bar-shaped slide section.

5. A guidewire catheter according to claim 4, wherein
   the click section projects outward with respect to a radial direction of the slide section to limit a movement of the slide section relative to the receiver when the click section contacts a proximal end section of the receiver; and
   the click section is capable of elastically deforming inwardly with respect to the radial direction of the slide section such that friction produced between the click section and the receiver limits the extension or retraction of the operation section and the guidewire adaptor.

6. A guidewire catheter according to claim 2, wherein
   the guidewire adapter and the slide section are connected to each other in a perpendicular direction, and
   the slide section and the receiver are arranged on the line which is parallel with and offsets from the axial line of the guide wire.

* * * * *